(12) United States Patent
Heaton et al.

(10) Patent No.: US 8,287,507 B2
(45) Date of Patent: Oct. 16, 2012

(54) REDUCED PRESSURE INDICATOR FOR A REDUCED PRESSURE SOURCE

(75) Inventors: Keith Patrick Heaton, Poole (GB); Ian James Hardman, Bournemouth (GB); Richard Daniel John Couthard, Verwood (GB); Timothy Mark Robinson, Basingstoke (GB); Christopher Brian Locke, Bournemouth (GB); Aidan Marcus Tout, Nomansland (GB); Benjamin Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 569 days.

(21) Appl. No.: 12/434,579

(22) Filed: May 1, 2009

(65) Prior Publication Data

US 2009/0254066 A1    Oct. 8, 2009

Related U.S. Application Data

(63) Continuation-in-part of application No. 11/974,534, filed on Oct. 15, 2007, now Pat. No. 8,007,257, and a continuation-in-part of application No. 12/069,262, filed on Feb. 8, 2008.

(60) Provisional application No. 60/851,494, filed on Oct. 13, 2006, provisional application No. 60/900,555, filed on Feb. 9, 2007, provisional application No. 61/050,107, filed on May 2, 2008.

(51) Int. Cl.
*A61M 1/00* (2006.01)
*A61M 27/00* (2006.01)
(52) U.S. Cl. ......... 604/316; 604/313; 604/315; 604/543
(58) Field of Classification Search .................. 604/315, 604/316, 543
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,084,691 | A | 4/1963 | Stoner |
| 3,367,332 | A | 2/1968 | Groves |
| 3,376,868 | A | 4/1968 | Mondiadis |

(Continued)

FOREIGN PATENT DOCUMENTS

AU    550575 A1    8/1982

(Continued)

OTHER PUBLICATIONS

Restriction Requirement date mailed Apr. 28, 2010 in U.S. Appl. No. 12/069,262.

(Continued)

*Primary Examiner* — Tatyana Zalukaeva
*Assistant Examiner* — Susan Su

(57) ABSTRACT

A reduced pressure apparatus includes a first casing portion and a second casing portion slidably coupled to the first casing portion such that the first casing portion is compressible into a plurality of positions relative to the second casing portion. The plurality of positions includes a fully compressed position and a fully uncompressed position. An indicator is disposed on at least one of the first casing portion and the second casing portion, the indicator being exposed when the first casing portion is in the fully uncompressed position.

19 Claims, 13 Drawing Sheets

U.S. PATENT DOCUMENTS

| | | |
|---|---|---|
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,779,243 A | 12/1973 | Tussey et al. |
| 3,826,254 A | 7/1974 | Mellor |
| 3,875,941 A | 4/1975 | Adair |
| 4,080,970 A | 3/1978 | Miller |
| 4,096,853 A | 6/1978 | Weigand |
| 4,098,434 A * | 7/1978 | Uhlig ............................ 222/94 |
| 4,132,332 A | 1/1979 | Wassilieff |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,278,089 A | 7/1981 | Huck et al. |
| 4,284,079 A | 8/1981 | Adair |
| 4,297,995 A | 11/1981 | Golub |
| 4,333,468 A | 6/1982 | Geist |
| 4,372,297 A | 2/1983 | Perlin |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,404,924 A | 9/1983 | Goldberg et al. |
| 4,419,097 A | 12/1983 | Rowland |
| 4,460,354 A | 7/1984 | Weilbacher et al. |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,578,060 A | 3/1986 | Huck et al. |
| 4,605,399 A | 8/1986 | Weston et al. |
| 4,608,041 A | 8/1986 | Nielsen |
| 4,640,688 A | 2/1987 | Hauser |
| 4,642,088 A | 2/1987 | Gunter |
| 4,643,719 A | 2/1987 | Garth et al. |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,798,583 A | 1/1989 | Beck et al. |
| 4,826,494 A | 5/1989 | Richmond et al. |
| 4,828,546 A | 5/1989 | McNeil et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,903,726 A | 2/1990 | Martin et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,019,059 A | 5/1991 | Goldberg et al. |
| 5,024,653 A | 6/1991 | Kohnke |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,102,404 A | 4/1992 | Goldberg et al. |
| 5,112,323 A | 5/1992 | Winkler et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,226,877 A | 7/1993 | Epstein |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,304,129 A | 4/1994 | Forgach |
| 5,318,548 A | 6/1994 | Filshie |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,542,939 A * | 8/1996 | Onodera et al. ............... 604/319 |
| 5,549,584 A | 8/1996 | Gross |
| 5,554,011 A | 9/1996 | Bales et al. |
| 5,556,375 A | 9/1996 | Ewall |
| 5,592,948 A | 1/1997 | Gatten |
| 5,607,388 A | 3/1997 | Ewall |
| 5,636,643 A | 6/1997 | Argenta et al. |
| 5,645,081 A | 7/1997 | Argenta et al. |
| 5,645,540 A | 7/1997 | Henniges et al. |
| 5,714,696 A | 2/1998 | Yeamans |
| 5,718,355 A | 2/1998 | Garby et al. |
| 5,819,990 A * | 10/1998 | Cimentepe et al. ........... 222/207 |
| 5,827,246 A | 10/1998 | Bowen |
| 5,830,198 A | 11/1998 | Henniges et al. |
| 6,024,731 A | 2/2000 | Seddon et al. |
| 6,071,267 A | 6/2000 | Zamierowski |
| 6,135,116 A | 10/2000 | Vogel et al. |
| 6,174,306 B1 | 1/2001 | Fleischmann |
| 6,241,747 B1 | 6/2001 | Ruff |
| 6,261,276 B1 | 7/2001 | Reitsma |
| 6,287,316 B1 | 9/2001 | Agarwal et al. |
| 6,345,623 B1 | 2/2002 | Heaton et al. |
| 6,485,007 B1 * | 11/2002 | Duelli ........................... 267/164 |
| 6,488,643 B1 | 12/2002 | Tumey et al. |
| 6,493,568 B1 | 12/2002 | Bell et al. |
| 6,553,998 B2 | 4/2003 | Heaton et al. |
| 6,626,891 B2 | 9/2003 | Ohmstede |
| 6,648,862 B2 | 11/2003 | Watson |
| 6,656,149 B2 | 12/2003 | Ladd |
| 6,745,765 B2 | 6/2004 | Kullik et al. |
| 6,814,079 B2 | 11/2004 | Heaton et al. |
| 6,979,324 B2 | 12/2005 | Bybordi et al. |
| 7,004,915 B2 | 2/2006 | Boynton et al. |
| 7,070,584 B2 | 7/2006 | Johnson et al. |
| 7,625,362 B2 | 12/2009 | Boehringer et al. |
| 8,007,257 B2 | 8/2011 | Heaton |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0198504 A1 | 12/2002 | Risk, Jr. et al. |
| 2003/0040687 A1 | 2/2003 | Boynton et al. |
| 2004/0064132 A1 | 4/2004 | Boehringer et al. |
| 2004/0243105 A1 | 12/2004 | Swan et al. |
| 2005/0004534 A1 * | 1/2005 | Lockwood et al. ........... 604/304 |
| 2005/0070858 A1 | 3/2005 | Lockwood et al. |
| 2005/0087556 A1 | 4/2005 | Signorini |
| 2005/0137539 A1 | 6/2005 | Biggie et al. |
| 2005/0197639 A1 | 9/2005 | Mombrinie |
| 2005/0261642 A1 | 11/2005 | Weston |
| 2005/0261643 A1 | 11/2005 | Bybordi et al. |

| | | | |
|---|---|---|---|
| 2006/0025727 | A1 | 2/2006 | Boehringer et al. |
| 2006/0216171 | A1 | 9/2006 | Hernandez |
| 2006/0229586 | A1 | 10/2006 | Faries, Jr. |
| 2007/0214692 | A1* | 9/2007 | Ferrara ........................ 40/324 |
| 2008/0183156 | A1 | 7/2008 | Yoo |
| 2008/0306456 | A1 | 12/2008 | Riesinger |

FOREIGN PATENT DOCUMENTS

| | | |
|---|---|---|
| AU | 745271 | 4/1999 |
| AU | 755496 | 2/2002 |
| CA | 2005436 | 6/1990 |
| CN | 2142728 Y | 9/1993 |
| CN | 1571682 A | 1/2005 |
| CN | 2745582 Y | 12/2005 |
| CN | 2829771 Y | 10/2006 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 60050296 A | 3/1985 |
| JP | 4129536 | 4/1992 |
| SG | 71559 | 4/2002 |
| WO | WO 80/02182 | 10/1980 |
| WO | WO 87/04626 | 8/1987 |
| WO | WO 90/010424 | 9/1990 |
| WO | WO 93/009727 | 5/1993 |
| WO | WO 94/020041 | 9/1994 |
| WO | WO 96/05873 | 2/1996 |
| WO | WO 97/18007 | 5/1997 |
| WO | WO 99/13793 | 3/1999 |
| WO | WO 2006/114648 A2 | 11/2006 |
| WO | WO 2007/013064 A1 | 2/2007 |
| WO | WO 2007/133618 A2 | 11/2007 |
| WO | WO 2009/135171 A2 | 11/2009 |

OTHER PUBLICATIONS

Response filed May 18, 2010 to Restriction Requirement dated Apr. 28, 2010 in U.S. Appl. No. 12/069,262.
Partial Search Report date mailed Jul. 21, 2010 for PCT Application No. PCT/US2009/050126.
Final Office Action date mailed Dec. 29, 2010 for U.S. Appl. No. 12/069,262.
Interview Summary date mailed Feb. 18, 2011 for U.S. Appl. No. 12/069,262.
Response filed Feb. 24, 2011 U.S. Appl. No. 12/069,262.
Advisory Action date mailed Mar. 7, 2011 U.S. Appl. No. 12/069,262.
RCE/Response filed Mar. 21, 2011 U.S. Appl. No. 12/069,262.
Final Office Action date mailed Feb. 16, 2011 for U.S. Appl. No. 11/974,534.
Response filed Mar. 29, 2011 for U.S. Appl. No. 11/974,534.
International Search Report and Written Opinion date mailed Jun. 30, 2008; PCT Application No. PCT/US2008/001727.
NPD 1000 Negative Pressure Wound Therapy System, Kalypto Medical Sep. 2008, pp. 1-4.
International Search Report and Written Opinion date mailed Sep. 11, 2009; PCT Application No. PCT/US2009/042598.
Restriction Requirement date mailed May 21, 2010 in U.S. Appl. No. 11/974,534.
Response to Restriction Requirement filed Jun. 21, 2010 in U.S. Appl. No. 11/974,534.
Non-Final Office Action date mailed Jul. 21, 2010 in U.S. Appl. No. 12/069,262.
Notice of Allowance date mailed Apr. 28, 2011 for U.S. Appl. No. 11/974,534.

N.A. Bagautdinov, "Variant of External Vacuum Aspiration in the Treatment of Purulent Diseases of the Soft Tissues," Current Problems in Modem. Clinical Surgery: Interdepartmental Collection, edited by V. Ye Volkov et. al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: "New and Established Methods, *Chronic Wound Care*, edited by D. Krasner (Health Management Publications, Inc., King of Prussia, PA 1990), pp. 240-246.

G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen,"*British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties*: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Non-Final Office Action date mailed Sep. 1, 2010 for U.S. Appl. No. 11/974,534.

Response filed Nov. 30, 2010 for U.S. Appl. No. 11/974,534.

Response filed Oct. 20, 2010 for U.S. Appl. No. 12/069,262.

Interview Summary date mailed Oct. 22, 2010 for U.S. Appl. No. 12/069,262.

Restriction Requirement date mailed Sep. 30, 2011 for U.S. Appl. No. 12/434,475.

Response filed Oct. 24, 2011 for U.S. Appl. No. 12/434,475.

\* cited by examiner

REDUCED PRESSURE INDICATOR FOR A REDUCED PRESSURE SOURCE

CROSS-REFERENCE TO RELATED APPLICATIONS

This application is a continuation-in-part application of U.S. patent application Ser. No. 11/974,534, filed Oct. 15, 2007 now U.S. Pat. No. 8,007,257, which claims the benefit U.S. Provisional Application No. 60/851,494, filed Oct. 13, 2006; this application is a continuation-in-part application of U.S. patent application Ser. No. 12/069,262, filed Feb. 8, 2008, which claims the benefit U.S. Provisional Application No. 60/900,555, filed Feb. 9, 2007; this application claims the benefit of U.S. Provisional Application No. 61/050,107, filed May 2, 2008. All of the above-referenced applications are hereby incorporated by reference.

BACKGROUND

1. Field of the Invention

The present invention relates generally to the field of tissue treatment, and more specifically to a system and method for applying reduced pressure at a tissue site.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure has involved treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times, Typically, reduced pressure is applied to tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment.

SUMMARY

The problems presented by existing reduced pressure systems are solved by the systems and methods of the illustrative embodiments described herein. In one illustrative embodiment, a reduced pressure apparatus includes a first casing portion and a second casing portion, the second casing portion being slidably coupled to the first casing portion such that the first casing portion is compressible into a plurality of positions relative to the second casing portion. The plurality of positions includes a fully compressed position and a fully uncompressed position. An indicator is disposed on at least one of the first casing portion and the second casing portion, the indicator being exposed when the first casing portion is in the fully uncompressed position.

In another embodiment, a reduced pressure therapy system for administering reduced pressure treatment to a tissue site includes a manifold adapted to be positioned at the tissue site, a reduced pressure source in fluid communication with the manifold to deliver a reduced pressure to the manifold, and a sealing member adapted to cover the tissue site to form a sealed space between the sealing member and the tissue site, the sealed space being in fluid communication with the reduced pressure source. The reduced pressure source includes a top casing portion and a bottom casing portion, the bottom casing portion being slidably coupled to the top casing portion such that the top casing portion is positionable in a plurality of positions relative to the bottom casing portion. The plurality of positions includes a fully compressed position, a fully uncompressed position, and a plurality of intermediate positions between the fully compressed position and the fully uncompressed position. The reduced pressure source is operable to deliver the reduced pressure when the top casing portion is in the fully compressed position. The reduced pressure source further includes an indicator disposed on at least one of the top casing portion and the bottom casing portion. The indicator is exposed when the top casing portion is in at least one of the plurality of intermediate positions.

In yet another embodiment, a reduced pressure apparatus includes a substantially cylindrical top casing portion and a substantially cylindrical bottom casing portion. The substantially cylindrical bottom casing portion has a larger diameter than the substantially cylindrical top casing portion. The substantially cylindrical top casing portion is slidably received by the substantially cylindrical bottom casing portion such that the substantially cylindrical top casing portion is positionable in a plurality of positions relative to the substantially cylindrical bottom casing portion. The plurality of positions includes a fully compressed position, a fully uncompressed position, and a plurality of intermediate positions between the fully compressed position and the fully uncompressed position. The reduced pressure apparatus is operable to deliver a reduced pressure as the substantially cylindrical top casing portion moves from the fully compressed position to the fully uncompressed position. The reduced pressure apparatus further includes a color strip disposed on the substantially cylindrical top casing portion such that the color strip is exposed when the substantially cylindrical top casing portion is in the fully uncompressed position and is obscured when the substantially cylindrical top casing portion is in the fully compressed position.

Other objects, features, and advantages of the illustrative embodiments will become apparent with reference to the drawings and detailed description that follow.

BRIEF DESCRIPTION OF THE DRAWINGS

FIG. 17c shows a reduced pressure therapy system that utilizes the apparatus shown in FIG. 17a;

DETAILED DESCRIPTION OF THE ILLUSTRATIVE EMBODIMENTS

Figure 1:
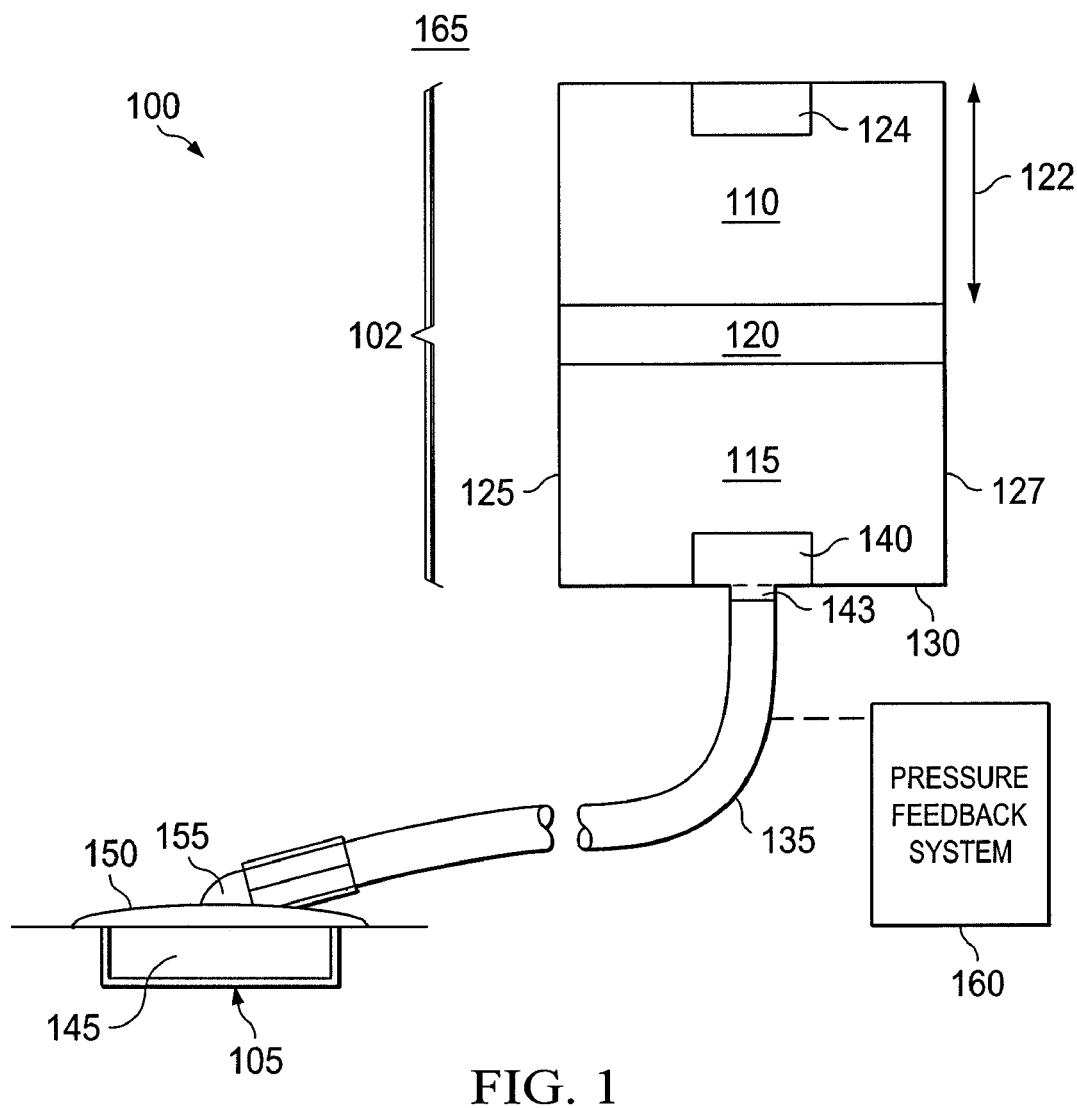
FIG. 1 illustrates a block diagram of an apparatus for applying reduced pressure at a tissue site in accordance with an illustrative embodiment.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the present invention is defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Reduced pressure treatment systems are often applied to large, highly exudating wounds present on patients undergoing acute or chronic care, as well as other severe wounds that are not readily susceptible to healing without application of reduced pressure. Low-severity wounds that are smaller in volume and produce less exudate have generally been treated using advanced dressings instead of reduced pressure treatment.

Currently, the use of reduced pressure treatment is not considered a viable or affordable option for low-severity wounds due to the manpower required to monitor and change system components, the requirement for trained medical personnel overseeing treatment, and the high cost of treatment. For example, the complexity of current reduced pressure treatment systems precludes a person with little or no specialized knowledge from administering such treatment to oneself or others. The size and power consumption characteristics of current reduced pressure treatment systems also limit the mobility of both the treatment system and the person to whom the treatment is being applied. Also, the high cost of current reduced pressure treatment systems can preclude the accessibility of such treatment systems to some users. Current reduced pressure treatment systems are also typically non-disposable after each treatment. In addition, users with little or no specialized knowledge have no easy and convenient way to determine whether a manually actuated reduced pressure source requires attention to maintain a desired reduced pressure level at a tissue site.

Referring to FIG. 1, a reduced pressure treatment system 100 according to an illustrative embodiment applies reduced pressure to a tissue site 105 to promote the drainage of exudate and other liquids from tissue site 105, as well as stimulate the growth of additional tissue. Reduced pressure treatment system 100 includes a pump 102. Pump 102 includes a variable volume chamber 110 and a fixed volume chamber 115, which are coupled to one another via filter housing 120. Variable volume chamber 10 has a variable volume that is affected by the compression of compressible pump along an axis 122. Variable volume chamber 110 may also be compressed along other axes.

Variable volume chamber 10 may be manually-actuated. That is, the compression of variable volume chamber 10 may be performed by any living organism. For example, variable volume chamber 10 may be manually pushed, squeezed, or otherwise compressed by a human hand, finger, or other limb. Variable volume chamber 10 may be any type of manually-actuated chamber. For example, variable volume chamber 110 may be a compressible bellows having corrugated side walls.

In one embodiment, variable volume chamber 110 is compressible into a plurality of positions, each of which may be representative of a different volume for variable volume chamber 110. For example, variable volume chamber 110 has the greatest volume when the variable volume chamber 110 is in a fully uncompressed position. In a fully compressed position, variable volume chamber 110 has the smallest volume. Variable volume chamber 110 may also have a plurality of intermediate positions between the fully uncompressed position and the fully compressed position, including partially compressed or partially uncompressed positions.

Variable volume chamber 110 includes an outlet valve 124. Outlet valve 124 permits the passage of gas, such as air, out of variable volume chamber 110. Outlet valve 124 also prevents gas from entering variable volume chamber 110. Thus, when the volume of variable volume chamber 110 is reduced due to the compression of compressible pump from an uncompressed position to a compressed position, gas is forced out of variable volume chamber 110. Outlet valve 124 may be any type of valve capable of permitting the passage of gas out of variable volume chamber 110 while preventing the passage of gas into variable volume chamber 110. A non-limiting example of outlet valve 124 is an umbrella valve, duckbill valve, ball valve, diaphragm valve, and any type of one-way valve.

Although FIG. 1 shows variable volume chamber 110 as having a single outlet valve 124, variable volume chamber 110 may have any number of outlet valves. Also, although FIG. 1 shows outlet valve 124 at the end portion of variable volume chamber 110, outlet valve 124 may be located on any portion of variable volume chamber 110, such as the side walls of variable volume chamber 110. In one embodiment, outlet valve 124 is located at an end of variable volume chamber 110 that is opposite of the end at which filter housing 120 is located. Additional details regarding outlet valve 124 will be provided in FIGS. 2, 7, and 9-13 below.

Fixed volume chamber 115 is capable of containing any fluid, such as gases and liquids, as well as fluids that contain solids. For example, fixed volume chamber 115 may contain exudates from tissue site 105. In one example, fixed volume chamber 115 has a substantially fixed volume. Fixed volume chamber 115 may be made of any material capable of providing fixed volume chamber 115 with a substantially fixed volume, including metal, plastic, or hardened rubber.

Fixed volume chamber 115 includes side walls 125 and 127, which are coupled to an end wall 130. Side walls 125 and 127 may be contiguously formed with an end wall 130 such that no joint exists between side walls 125 and 127 and end wall 130. In addition, side walls 125 and 127 may be welded, screwed, glued, bolted, air-lock sealed, or snapped onto end wall 130.

Fixed volume chamber 115 is coupled to variable volume chamber 110 by a filter housing 120. Fixed volume chamber 115 and variable volume chamber 110 may be coupled to filter housing 120 in a variety of ways. For example, fixed volume chamber 115 or variable volume chamber 110 may be welded, screwed, glued, bolted, air-lock sealed, or snapped onto filter housing 120. Fixed volume chamber 115 or variable volume chamber 110 may also be part of the same material as filter housing 120, thereby eliminating the need for joints or seals between fixed volume chamber 115 and filter housing 120. In another example, variable volume chamber 110 may be sealed to filter housing 120 using an interlocking seal. Additional details regarding the coupling of filter housing 120 with fixed volume chamber 115 or variable volume chamber 110 are described below in FIGS. 2, 5, 6, 10-13, and 14.

Filter housing 120 is capable of including one or more filters. In one embodiment, filter housing 120 includes a hydrophobic filter that prevents liquid from entering variable volume chamber 110 from fixed volume chamber 115. However, as described below, the hydrophobic filter permits the passage of air such that reduced pressure may be transferred from variable volume chamber 110 to fixed volume chamber 115. Filter housing 120 may also include an odor filter that restrains or prevents the transmission of odor from fixed volume chamber 115 to variable volume chamber 110. Additional details regarding the hydrophobic filter and odor filter will be provided in FIGS. 2, 4, and 14 below.

Fixed volume chamber 115 is coupled to a delivery tube 135 via an inlet valve 140. Inlet valve 140 is located at an inlet point 143. Inlet valve 140 permits the passage of fluid, such as exudate, into fixed volume chamber 115 at inlet point 143. Inlet valve 140 also restrains the passage of fluid out of fixed volume chamber 115 at inlet point 143. Inlet valve 140 may be any type of valve, such as an umbrella valve, duck bill valve, or a combination thereof.

Inlet valve 140 may be located at the center of end wall 130. Although FIG. 1 shows fixed volume chamber 115 as having a single inlet valve 140, fixed volume chamber 115 may have any number of inlet valves. Also, although FIG. 1 shows inlet valve 140 at end wall 130 of fixed volume chamber 115, inlet valve 140 may be located on any portion of fixed volume chamber 115, such as side walls 125 and 127 of fixed volume chamber 115. Additional details regarding inlet valve 140 will be provided in FIGS. 2 and 17 below.

Delivery tube 135 is any tube through which a fluid may flow. Delivery tube 135 may be made from any material, and may include one or more paths or lumens through which fluid may flow. For example, delivery tube 135 may include two lumens. In this example, one lumen may be used for the passage of exudate from tissue site 105 to fixed volume chamber 115. The other lumen may be used to deliver fluids, such as air, antibacterial agents, antiviral agents, cell-growth promotion agents, irrigation fluids, or other chemically active agents, to tissue site 105. The fluid source from which these deliverable fluids originate is not shown in FIG. 1.

Delivery tube 135 may be fixedly attached to fixed volume chamber 115 at inlet point 143. Also, delivery tube 135 may be detachable from fixed volume chamber 115 at inlet point 143. For example, delivery tube 135 may be snapped onto fixed volume chamber 115. Additional details regarding the coupling the delivery tube 135 to fixed volume chamber 115 will be provided in FIGS. 2 and 16-18 below.

The opposite end of delivery tube 135 is coupled to a manifold 145. Manifold 145 may be a biocompatible, porous material that is capable of being placed in contact with tissue site 105 and distributing reduced pressure to the tissue site 105. Manifold 145 may be made from foam, gauze, felted mat, or any other material suited to a particular biological application. Manifold 145 may include a plurality of flow channels or pathways to facilitate distribution of reduced pressure or fluids to or from the tissue site.

Manifold 145 may be secured to tissue site 105 using a sealing member 150. Sealing member 150 may be a cover that is used to secure manifold 145 at tissue site 105. While sealing member 150 may be impermeable or semi-permeable, in one example sealing member 150 is capable of maintaining a reduced pressure at tissue site 105 after installation of the sealing member 150 over manifold 145. Sealing member 150 may be a flexible drape or film made from a silicone based compound, acrylic, hydrogel or hydrogel-forming material, or any other biocompatible material that includes the impermeability or permeability characteristics desired for tissue site 105.

In one embodiment, sealing member 150 is configured to provide a sealed connection with the tissue surrounding manifold 145 and tissue site 105. The sealed connection may be provided by an adhesive positioned along a perimeter of sealing member 150 or on any portion of sealing member 150 to secure sealing member 150 to manifold 145 or the tissue surrounding tissue site 105. The adhesive may be pre-positioned on sealing member 150 or may be sprayed or otherwise applied to sealing member 150 immediately prior to installing sealing member 150.

In one embodiment, delivery tube 135 is coupled to manifold 145 via a connection member 155. Connection member 155 permits the passage of fluid from manifold 145 to delivery tube 135, and vice versa. For example, exudates collected from tissue site 105 using manifold 145 may enter delivery tube 135 via connection member 155. In another embodiment, reduced pressure treatment system 100 does not include connection member 155. In this embodiment, delivery tube 135 may be inserted directly into sealing member 150 such that an end of delivery tube 135 is adjacent to manifold 145.

Reduced pressure treatment system 100 may also include a pressure feedback system 160. Pressure feedback system 160 may be operably associated with the other components of reduced pressure treatment system 100 to provide information to a user of reduced pressure treatment system 100 that indicates a relative or absolute amount of pressure that is being delivered to tissue site 105. Pressure feedback system 160 allows a user to accurately track the amount of reduced pressure that is being generated by reduced pressure treatment system 100. Non-limiting examples of pressure feedback systems include pop valves that activate when the reduced pressure rises above a selected value, low power electronic indicators powered by miniature cells, dial indicators that indicate specific pressure values that are being applied to the tissue site, deflection pop valves, polymers with various deflection characteristics, and films that move relative to one another to produce visual identifiers indicating the relative or absolute pressure values being generated by reduced pressure treatment system 100. An example of a film-based system may include a yellow film anchored to a first part of pump 102 that is capable of movement relative to a blue film anchored to a second part. When the first and second parts are moved relative to one another to apply a reduced pressure, the yellow and blue films overlap to create a green indicator. As the pressure increases and the films move away from one another, the loss of the green color indicates that the pressure has increased (i.e., more reduced pressure needs to be applied).

Also, although pressure feedback system 160 is shown as separate from the other components of reduced pressure treatment system 100, pressure feedback system 160 may form an integral part of any of the components of reduced pressure treatment system 100. Additional details regarding pressure feedback system 160 will be described in FIGS. 14 and 16 below. In addition to the above-mentioned components and systems, reduced pressure treatment system 100 may include valves, regulators, switches, and other electrical, mechanical, and fluid components to facilitate administration of reduced pressure treatment to tissue site 105.

A desiccant or absorptive material may be disposed within fixed volume chamber 115 to trap or control fluid once the fluid has been collected. In the absence of fixed volume chamber 115, a method for controlling exudate and other fluids may be employed in which the fluids, especially those that are water soluble, are allowed to evaporate from manifold 145.

In one embodiment, variable volume chamber 110 is moved from an uncompressed position to a compressed position, thereby decreasing the volume of variable volume chamber 110. As a result, gas is expelled from variable volume chamber 110 through outlet valve 124. Because gas cannot enter variable volume chamber 110 via outlet valve 124, gas cannot enter variable volume chamber 110 from a surrounding space 165. Thus, as variable volume chamber 110 expands from the compressed position to the uncompressed position, gas is transferred from fixed volume chamber 115 to variable volume chamber 110. The movement of variable volume chamber 110 from a compressed position to an uncompressed position may be caused by any expansion force. In an illustrative example in which the side walls of variable volume chamber 110 are corrugated side walls, the expansion force may be caused by the tendency of the corrugations in the corrugated side walls to move away from one another and thereby return variable volume chamber 110 to the uncompressed position. The expansion force may also be caused by an independent biasing member, such as a spring or foam component, that is located within or outside of variable volume chamber 110. In another example, the resiliency of non-corrugated side walls of variable volume chamber 110 may be used to move variable volume chamber 110 to an uncompressed position.

Liquid, such as exudate, is prevented from being transferred from fixed volume chamber 115 to variable volume chamber 110 by a filter, such as a hydrophobic filter, in filter housing 120. Because fixed volume chamber 115 is sealed from surrounding space 165, a reduced pressure is generated in fixed volume chamber 115 as variable volume chamber 110 expands from the compressed position to the uncompressed position. This reduced pressure is than transferred to tissue site 105 via delivery tube 135 and manifold 145. This reduced pressure may be maintained at tissue site 105 using sealing member 150.

This process of moving variable volume chamber 110 from an uncompressed to a compressed position, and vice versa, in order to achieve a reduced pressure at tissue site 105 may be repeated. In particular, variable volume chamber 110 may undergo multiple compression/expansion cycles until fixed volume chamber 115 is filled with liquid, such as exudate, from tissue site 105. The multi-chamber configuration of pump 102, which includes variable volume chamber 110 and fixed volume chamber 115, permits compressible pump to be compressed regardless of the amount of liquid in fixed volume chamber 115. As a result, the desired pressure may be achieved during the compression/expansion cycles regardless of the amount of liquid in fixed volume chamber 115.

Figure 2:
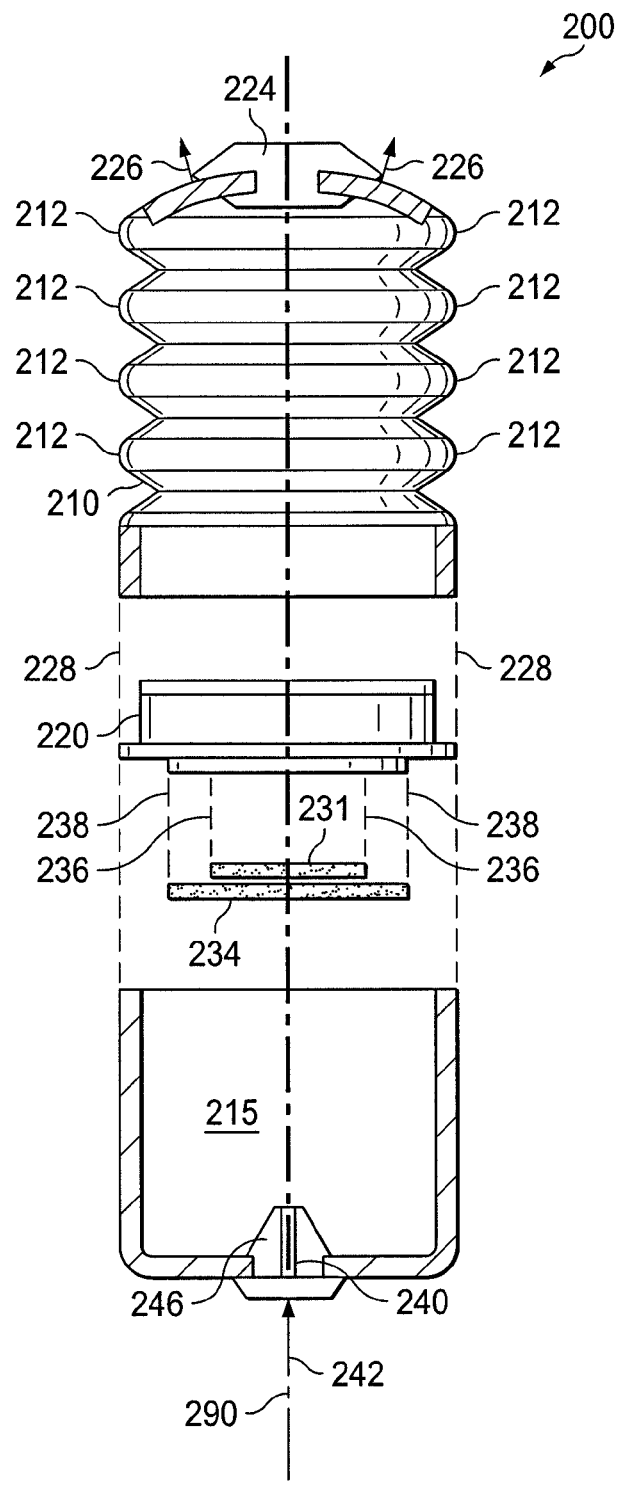
FIG. 2 illustrates a cross-sectional view of an apparatus for applying reduced pressure at a tissue site in accordance with an illustrative embodiment.

Referring to FIG. 2, pump 200, which is a non-limiting example of pump 102 in FIG. 1, is shown in accordance with an illustrative embodiment. Pump 200 may be used as a substitute for pump 102 in FIG. 1.

Pump 200 includes a compressible bellows 210. Compressible bellows 210 is a non-limiting example of variable volume chamber 110 in FIG. 1. Compressible bellows 210 may be moved into a plurality of positions, such as an uncompressed position and a compressed position. Compressible bellows 210 is formed from corrugated side walls with corrugations 212. Corrugations 212 may move toward and away from one another, resulting in a compression and expansion of compressible bellows 210. For example, compressible bellows 210 may move from a compressed position to an uncompressed position due to the expansion force provided by a decrease in the linear density of corrugations 212. This expansion force may be provided by the tendency of corrugations 212 to move away from one another.

In addition, compressible bellows 210 may be composed of any material that allows the compression and expansion of compressible bellows 210. The expansion force provided by the corrugated side walls may depend on the material from which compressible bellows 210 is composed. Thus, the amount of pressure provided by compressible bellows 210 to a tissue site, such as tissue site 105 in FIG. 1, may also depend on the material from which compressible bellows 210 is composed. Factors that may affect the amount of pressure provided by compressible bellows 210 include material hardness, elasticity, thickness, resiliency, and permeability. A material may also be selected based on the degree of pressure decay experienced by pump 200 as compressible bellows 210 moves from a compressed position to an uncompressed position. The expansion force provided by the corrugated side walls may also depend on the design of compressible bellows 210. The variance in cross-section of compressible bellows 210 affects the amount of obtainable reduced pressure as well as the input input pressure required to initiate compressible bellows 210.

In one non-limiting example, compressible bellows 210 is composed of Shore 65 A. Shore 65 A may be capable of providing between 125 and 150 mm Hg of pressure. These levels of pressure may also be capable of being maintained for at least six hours. For higher pressures, harder materials, such as Shore 85 A, may be used. By varying the material from which compressible bellows 210 is composed, pressures of 250 mm Hg, as well as pressures above 400 mm Hg, may by achieved using compressible bellows 210.

Although compressible bellows 210 is shown to have a circular cross-sectional shape, compressible bellows 210 may have any cross-sectional shape. For example, the cross sectional shape of compressible bellows 210 may be an oval or polygon, such as a pentagon, hexagon, or octagon.

Compressible bellows 210 includes outlet valve 224. Outlet valve 224 is a non-limiting example of outlet valve 124 in FIG. 1. Gas exits compressible bellows 210 via outlet valve 224 in response to a movement of compressible bellows 210 from an uncompressed position to a compressed position. Outlet valve 224 may be located anywhere on compressible bellows 210. For example, outlet valve 224 may be located on an end of compressible bellows 210 that is opposite of the end at which filter housing 220 is located. Outlet valve 224 may also be centrally disposed on an end wall of compressible bellows 210. The directional flow of the gas from compressible bellows 210 is indicated by arrows 226. Outlet valve 224 prevents gas from entering compressible bellows 210. In FIG. 2, outlet valve 224 is an umbrella valve, although outlet valve 224 may be any type of valve. Additional details regarding outlet valve 224 are described in FIG. 7 below.

As indicated by dotted lines 228, compressible bellows 210 is coupled to filter housing 220. Compressible bellows 210 may be welded, screwed, glued, bolted, air-lock sealed, or snapped onto filter housing 220. Additional details regarding the coupling between compressible bellows 210 and filter housing 220 are described in FIGS. 5 and 6 below.

Filter housing 220 is a non-limiting example of filter housing 120 in FIG. 1. Filter housing may be composed of any material, such as plastic, metal, rubber, or any other material capable of holding one or more filters. Filter housing 220 contains an odor filter 231, which is attached to filter housing 220 as indicated by dotted lines 236. Odor filter 231 may be screwed, glued, bolted, air-lock sealed, snapped onto, or otherwise placed adjacent to filter housing 220. Also, filter housing 220 may include a groove into which odor filter 231 is placed.

Odor filter 231 restrains or prevents the transmission of odor from fixed volume chamber 215 to compressible bellows 210. Such odor may be the result of exudate or other liquid contained in fixed volume chamber 215. In one embodiment, odor filter 231 is a carbon odor filter. In this embodiment, the carbon odor filter may include charcoal. Although FIG. 2 depicts odor filter 231 as a having a flattened shape, odor filter 231 may have any shape capable of restraining or preventing the transmission of odor from fixed volume chamber 215 to compressible bellows 210. For example, odor filter 231 may have circular, ovular, or polygonal disk shape.

Filter housing 220 also includes a hydrophobic filter 234, which is attached to filter housing 220 as indicated by dotted lines 238. Hydrophobic filter 234 may be screwed, glued, bolted, air-lock sealed, snapped onto, ultrasonically welded, or otherwise placed adjacent to filter housing 220. In one example, odor filter 231 is sandwiched between filter housing 220 and hydrophobic filter 234. In the example in which hydrophobic filter 234 is secured to filter housing 220, odor filter 231 may be secured as a result of being sandwiched between filter housing 220 and hydrophobic filter 234. Odor filter 231 and hydrophobic filter 234 may be coupled to a side of filter housing 220 that is nearer to fixed volume chamber 215, as shown in FIG. 2.

Hydrophobic filter 234 prevents liquid, such as exudate, from entering compressible bellows 210. However, hydrophobic filter 234 allows the passage of gas, such as air, such that reduced pressure may be transferred from compressible bellows 210 and fixed volume chamber 215. Hydrophobic filter 234 may be composed from any of a variety of materials, such as expanded polytetrafluoroethene.

Pump 200 includes fixed volume chamber 215. Fixed volume chamber 215 is a non-limiting example of fixed volume chamber 115 in FIG. 1. Fixed volume chamber 215 has a fixed volume and may contain any liquid, such as exudate from a tissue site, such as tissue site 105 in FIG. 1. Fixed volume chamber 215 may be welded, screwed, glued, bolted, air-lock sealed, or snapped onto filter housing 220.

Fixed volume chamber 215 includes inlet valve 240. Inlet valve 240 is a non-limiting example of inlet valve 140 in FIG. 1. As shown in FIG. 2, inlet valve 240 is centrally located at an end wall of fixed volume chamber 215. Also, inlet valve 240 and outlet valve 224 are each located along a central longitudinal axis 290, which traverses the center of pump 200.

Any liquid, such as exudate, may flow from a manifold, such as manifold 145 in FIG. 1, into fixed volume chamber 215 via inlet valve 240. The flow of liquid into fixed volume chamber 215 via inlet valve 240 is indicated by an arrow 242. Inlet valve 240 also restrains or prevents the passage of liquid out of fixed volume chamber 215 at the point at which inlet valve 240 is located.

Any of a variety of valves may be used to achieve the functionality of inlet valve 240. In one embodiment, top portion 246 of inlet valve 240 is a duck bill valve. Inlet valve 240 may also be an umbrella valve, duckbill valve, ball valve, diaphragm valve, and any type of one-way valve.

Liquid flow into fixed volume chamber 215 is caused by the reduced pressure in fixed volume chamber 215. The reduced pressure in fixed volume chamber 215 is caused by the reduced pressure transferred from compressible bellows 210 to fixed volume chamber 215. As compressible bellows 210 is moved from a compressed position to an uncompressed position, gas is transferred from fixed volume chamber 215 to compressible bellows 210. As a result, reduced pressure is transferred to fixed volume chamber 215 from compressible bellows 210 in response to a movement of compressible bellows 210 from a compressed position to an uncompressed position. As compressible bellows 210 is moved from an uncompressed position to a compressed position, gas moves out of compressible bellows 210 via outlet valve 224. Such compression/expansion cycles may be repeated to apply a desired amount of reduced pressure to a tissue site, such as tissue site 105 in FIG. 1.

Figure 3:
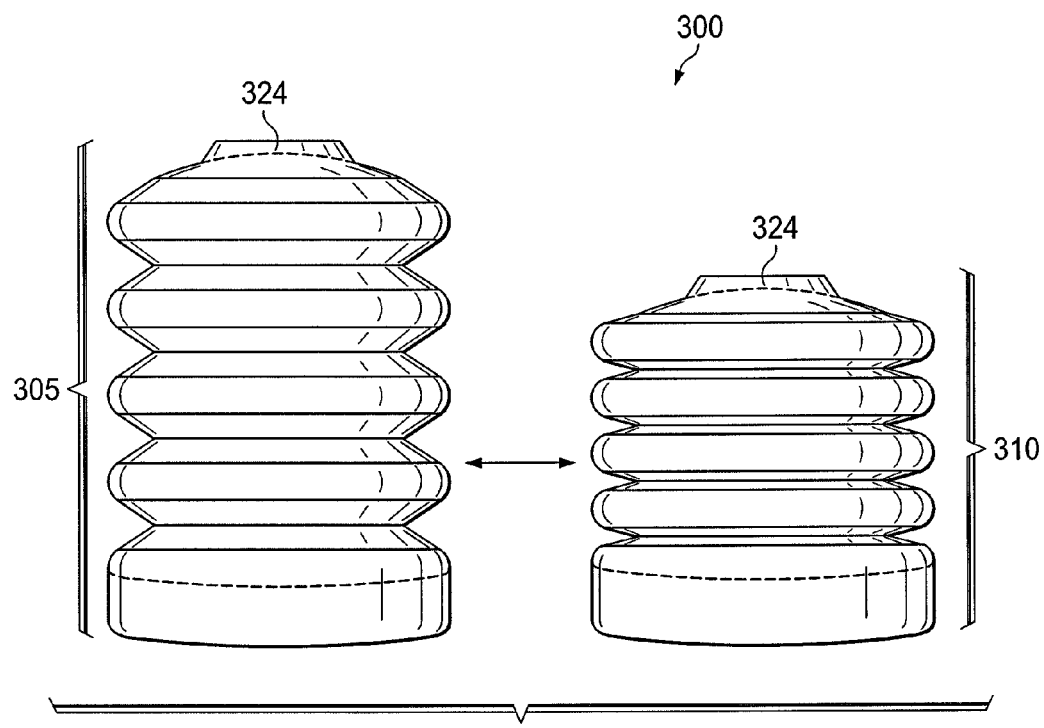
FIG. 3 illustrates a perspective view of a compressible pump in an apparatus for applying reduced pressure at a tissue site in accordance with an illustrative embodiment.

Referring to FIG. 3, compressible bellows 300, which is a non-limiting example of bellows pump 200 in FIG. 2, is shown in accordance with an illustrative embodiment. In FIG. 3, compressible bellows 300 is shown in two different positions in the range of positions that may be achieved by compressible bellows 300. In particular, compressible bellows 300 is shown in an uncompressed position 305 and a compressed position 310. Compressible bellows 300 has a greater volume in uncompressed position 305 than in compressed position 310.

As compressible bellows 300 is compressed from uncompressed position 305 to compressed position 310, the gas in compressible bellows 300 is expelled through outlet valve 324, which is a non-limiting example of outlet valve 224 in FIG. 2. The volume of compressible bellows 300 decreases as the compressible bellows 300 is compressed.

As compressible bellows 300 expands from compressed position 310 to uncompressed position 305, gas does not enter compressible bellows 300 via outlet valve 324 because outlet valve 324 allows air only to exit compressible bellows 300. Instead, gas enters bellows pump from a fixed volume chamber, such as fixed volume chamber 215 in FIG. 2, to which compressible bellows 300 is coupled. The volume of compressible bellows 300 increases as compressible bellows 300 expands from compressed position 310 to uncompressed position 305.

The expansion force necessary to expand compressible bellows 300 is provided by an expansion or biasing force. The material from which compressible bellows 300 is composed is elastically deformed when compressible bellows 300 is in compressed position 310. Elastic properties of the material from which compressible bellows 300 is composed biases the corrugations included on compressible bellows 300 to move away from one another such that compressible bellows 300 expands to uncompressed position 305. As compressible bellows 300 expands, the sealed nature of the variable volume chamber results in a reduced pressure being created within the variable volume chamber. The reduced pressure may then be transmitted through a hydrophobic filter to a fixed volume chamber, which, in turn, transmits the reduced pressure to a tissue site.

Figure 4:
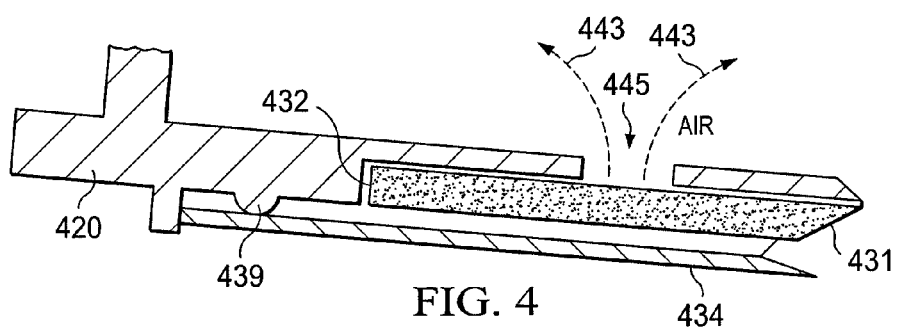
FIG. 4 illustrates a cross-sectional view of a filter housing in an apparatus for applying reduced pressure at a tissue site in accordance with an illustrative embodiment.

Referring to FIG. 4, a portion of filter housing 420, which is a non-limiting example of filter housing 220 in FIG. 2, is shown in accordance with an illustrative embodiment. Odor filter 431, which is a non-limiting example of odor filter 231 in FIG. 2, fits onto filter housing 420 at a groove 432. Hydrophobic filter 434, which is a non-limiting example of hydrophobic filter 234 in FIG. 2, is ultrasonically welded to filter housing 420 at a protrusion 439. However, as described above, hydrophobic filter 234 may be coupled to filter housing 420 in a variety of ways. Odor filter 431 is sandwiched in between filter housing 420 and hydrophobic filter 434 at groove 432, and may or may not be independently attached to filter housing 420.

As indicated by arrows 443, gas, such as air, is permitted to flow though hydrophobic filter 434 and odor filter 431, via a gap 445. However, hydrophobic filter 434 prevents liquid, such as exudate, from passing through gap 445. Also, odor filter 431 prevents odor from passing through gap 445.

Figure 5:
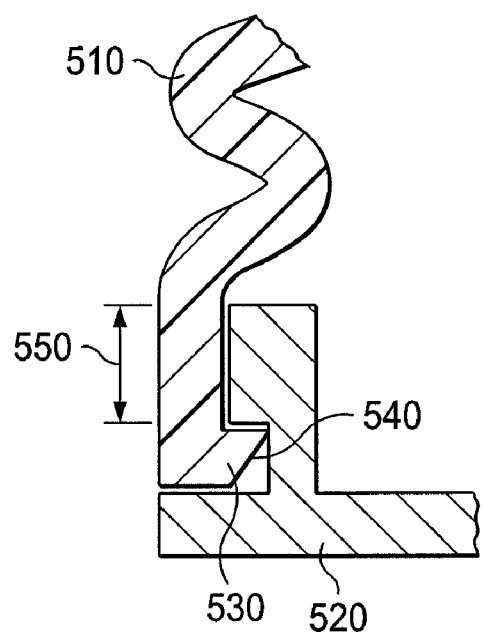
FIG. 5 illustrates a cross-sectional view of an interlocking seal in an apparatus for applying reduced pressure at a tissue site in accordance with an illustrative embodiment.

Referring to FIG. 5, an interlocking seal between compressible bellows 510, which is a non-limiting example of compressible bellows 210 in FIG. 2, and filter housing 520, which is a non-limiting example of filter housing 220 in FIG. 2, is shown in accordance with an illustrative embodiment. The interlocking seal shown in FIG. 5 allows compressible bellows 510 to be snapped onto filter housing 520, while maintaining an air-tight seal for the proper operation of the reduced pressure treatment system. Compressible bellows 510 includes a snap protrusion 530. Filter housing 520 includes an undercut 540 into which snap protrusion 530 may be inserted. The large area of contact between compressible bellows 510 and filter housing 520, as indicated by a span 550, assists in maintaining a proper seal between compressible bellows 510 and filter housing 520.

Figure 6:
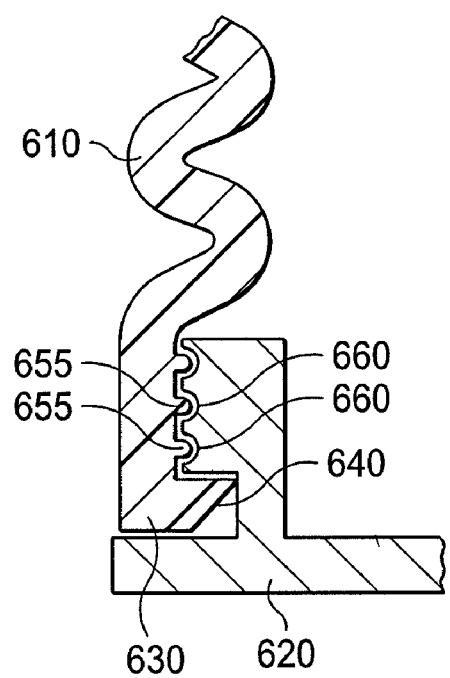
FIG. 6 illustrates a cross-sectional view of an interlocking seal in an apparatus for applying reduced pressure at a tissue site in accordance with an illustrative embodiment.

Referring to FIG. 6, an interlocking seal between compressible bellows 610, which is a non-limiting example of compressible bellows 210 in FIG. 2, and filter housing 620, which is a non-limiting example of filter housing 220 in FIG. 2, is shown in accordance with an illustrative embodiment. Similar to the interlocking seal in FIG. 5, filter housing 620 includes undercut 640 into which snap protrusion 630 of compressible bellows 610 may be inserted. However, in contrast to FIG. 5, the illustrative embodiment of the interlocking seal in FIG. 6 shows that compressible bellows 610 includes ribs 655. Filter housing 620 also includes indentations 660, into which ribs 655 may be inserted. The use of interlocking ribs 655 and indentations 660 may help create a tighter seal between compressible bellows 610 and filter housing 620.

Figure 7:
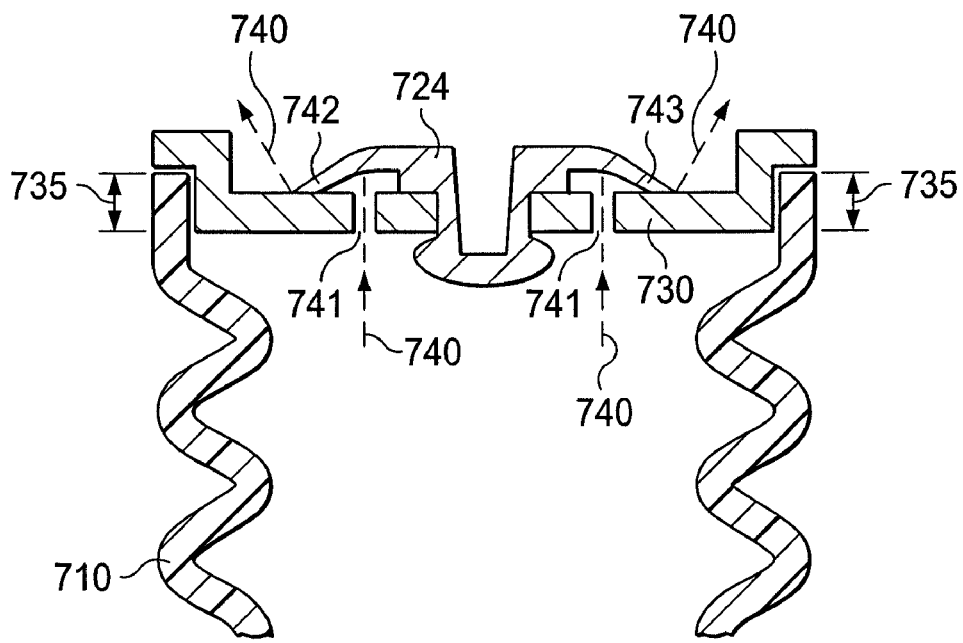
FIG. 7 illustrates a cross-sectional view of an outlet valve in an apparatus for applying reduced pressure at a tissue site in accordance with an illustrative embodiment.

Referring to FIG. 7, outlet valve 724, which is a non-limiting example of outlet valve 224 in FIG. 2, is shown in accordance with an illustrative embodiment. Outlet valve 724 is coupled to an end wall 730 of compressible bellows 710, which is a non-limiting example of compressible bellows 210 in FIG. 2. End wall 730 may be made of metal, plastic, rubber, or any other material. In FIG. 7, end wall 730 may be welded onto compressible bellows 710 at the spans indicated by spans 735. However, end wall 730 may also be screwed, glued, bolted, air-lock sealed, or snapped onto compressible bellows 710.

Gas, such as air, flows out of compressible bellows 710 as indicated by arrows 740. In particular, gas flows out of compressible bellows 710 through gaps 741 and then passes through the space between outlet valve flaps 742 and 743 and end wall 730. However, because outlet valve flaps 742 and 743 are only opened by the flow of gas out of compressible bellows 710, gas cannot enter compressible bellows 710 through outlet valve 724. In FIG. 7, outlet valve 724 is an umbrella valve. However, outlet valve 724 may be any valve capable of allowing gas to pass out of compressible bellows 710 while restraining or preventing gas from passing out of compressible bellows 710.

Figure 8:
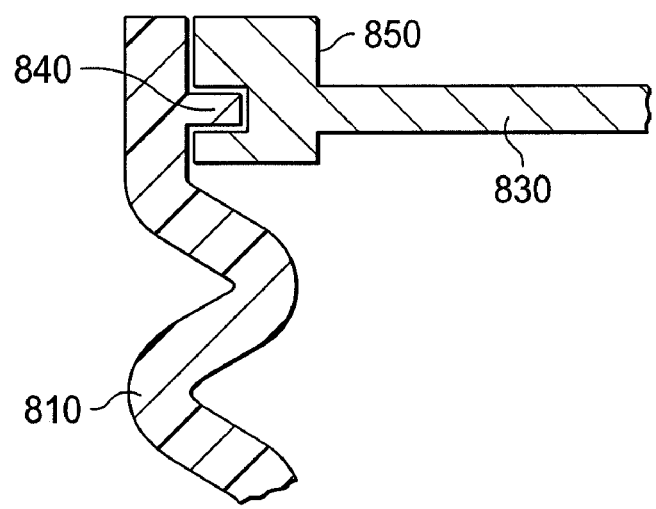
FIG. 8 illustrates a cross-sectional view of a connection joint in an apparatus for applying reduced pressure at a tissue site in accordance with an illustrative embodiment.

Referring to FIG. 8, a connection between end wall 830, which is a non-limiting example of end wall 730 in FIG. 7, and compressible bellows 810, which is a non-limiting example of compressible bellows 710 in FIG. 7, is shown in accordance with an illustrative embodiment. In contrast to FIG. 7, the illustrative embodiment of FIG. 8 shows a protrusion 840 included on compressible bellows 810. End wall 830 also includes an indentation 850 into which protrusion 840 may be inserted. The use of protrusion 840 and indentation 850 may help create a tighter seal between compressible bellows 810 and end wall 830, as well as help reduce the amount of welding necessary to couple compressible bellows 810 to end wall 830.

Figure 9:
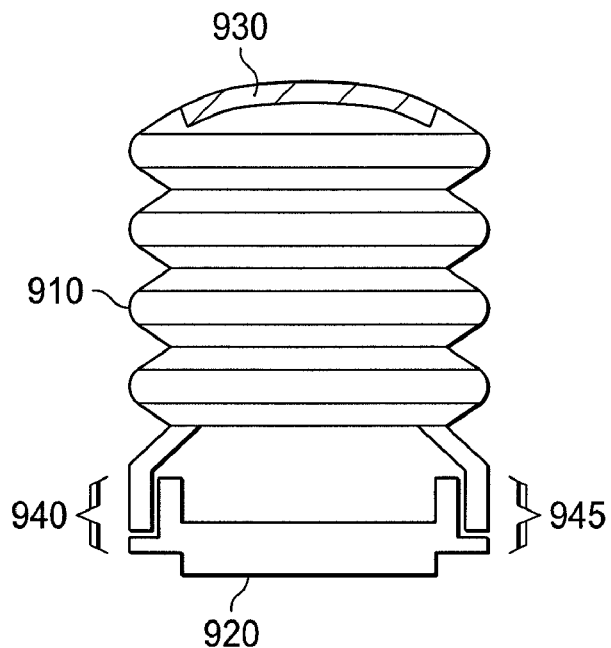
FIG. 9 illustrates a perspective view of outlet valves on a compressible pump in an apparatus for applying reduced pressure at a tissue site in accordance with an illustrative embodiment.

Referring to FIG. 9, compressible bellows 910, which is a non-limiting example of compressible bellows 210 in FIG. 2, is shown in accordance with an illustrative embodiment. Compressible bellows 910 is coupled to filter housing 920, which is a non-limiting example of filter housing 220 in FIG. 2. In FIG. 9, end wall 930 of compressible bellows 910 does not include an outlet valve. Instead, compressible bellows 910 includes outlet valves at the portions of compressible bellows 910 indicated by brackets 940 and 945. In addition, compressible bellows 910 may include one or more outlet valves around the perimeter of compressible bellows 910 indicated by brackets 940 and 945. Additional details regarding the outlet valves at the portion of compressible bellows 910 indicated by brackets 940 and 945 is described in FIGS. 10-13 below.

Figure 10:
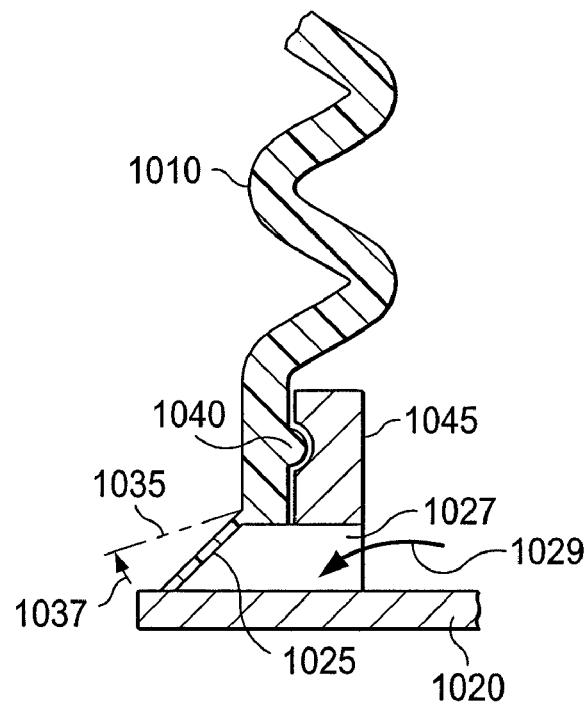
FIG. 10 illustrates a cross-sectional view of an outlet valve in an apparatus for applying reduced pressure at a tissue site in accordance with an illustrative embodiment.

Turning now to FIG. 10, an umbrella outlet valve that is part of compressible bellows 1010, which is a non-limiting example of compressible bellows 910 in FIG. 9, is shown in accordance with an illustrative embodiment. The outlet valve includes a flap 1025. Filter housing 1020, which is a non-limiting example of filter housing 920 in FIG. 9, includes a gap 1027. Upon moving compressible bellows 1010 from an uncompressed position to a compressed position, gas flows out of compressible bellows through gap 1027 as indicated by arrow 1029. The flow of gas lifts flap 1025 into open position 1035, as indicated by an arrow 1037, thereby allowing the passage of gas out of compressible bellows 1010. When air is not flowing out of compressible bellows 1010, such as when compressible bellows 1010 is moving from a compressed position to an uncompressed position, flap 1025 is in contact with filter housing 1020 such that gas may not flow into compressible bellows 1010.

In this embodiment, compressible bellows 1010 may also have protrusion 1040, which fits into indentation 1045 of filter housing 1020. The fitting of protrusion 1040 into indentation 1045 helps to maintain a snap fit between compressible bellows 1010 and filter housing 1020.

Figure 11:
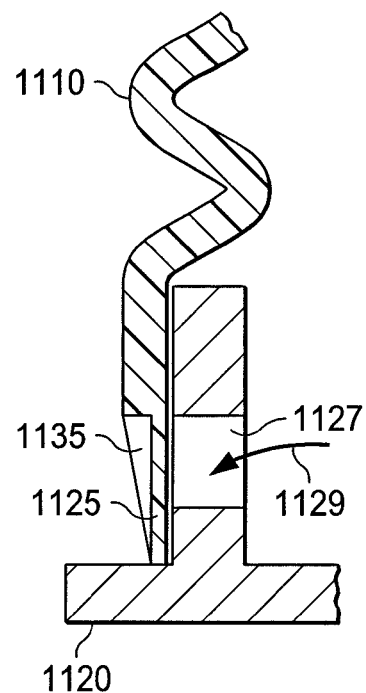
FIG. 11 illustrates a cross-sectional view of an outlet valve in an apparatus for applying reduced pressure at a tissue site in accordance with an illustrative embodiment.

Referring to FIG. 11, an outlet valve located on compressible bellows 1110 at the general portion of compressible bellows 1110 that contacts filter housing 1120 is shown in accordance with an illustrative embodiment. Compressible bellows 1110 is a non-limiting example of compressible bellows 910 in FIG. 9, and filter housing 1120 is a non-limiting example of filter housing 920 in FIG. 9.

Upon compression of compressible bellows 1110 from an uncompressed position to a compressed position, gas attempts to flow out of compressible bellows 1110 through gap 1127 as indicated by arrow 1129. The gas encounters flap 1125, which includes a rib 1135. The strength of rib 1135, which may depend on the thickness or material of rib 1135, determines the amount of force that must be exerted by the gas in order to bend flap 1125 such that air can escape compressible bellows 1110. Thus, the strength of rib 1135 also determines the amount of pressure that is created by compressible bellows 1110, and which is ultimately transferred to a tissue site, such as tissue site 105 in FIG. 1.

Figure 12:
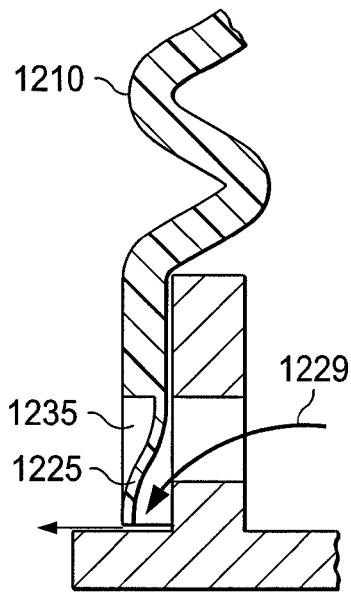
FIG. 12 illustrates a cross-sectional view of an outlet valve in an apparatus for applying reduced pressure at a tissue site in accordance with an illustrative embodiment.

Referring to FIG. 12, the outlet valve of FIG. 11 in an open position is shown in accordance with an illustrative embodiment. The flow of gas, which is indicated by arrow 1229, has exerted sufficient force upon flap 1225 of compressible bellows 1210 such that flap 1225 has been bent to allow for the release of gas from compressible bellows 1210. In particular, the force exerted by the flow of gas is sufficient to overcome the strengthening force of rib 1235.

Figure 13:
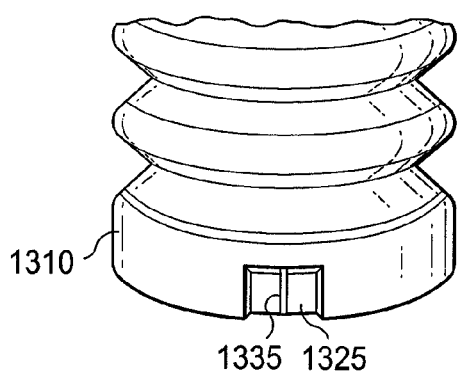
FIG. 13 illustrates a perspective view of an outlet valve in an apparatus for applying reduced pressure at a tissue site in accordance with an illustrative embodiment.

Referring to FIG. 13, an outlet valve located on a side wall of bellow pump 1310, which is a non-limiting example of compressible bellows 1110 and 1210 in FIGS. 11 and 12, respectively, is shown in accordance with an illustrative embodiment. FIG. 13 shows flap 1325, which is a non-limiting example of flaps 1125 and 1225 in FIGS. 11 and 12, respectively. FIG. 13 also shows rib 1335, which is a non-limiting example of ribs 1135 and 1235 in FIGS. 11 and 12, respectively. As described above, rib 1335 may be used to adjust the force required to open flap 1325, thereby varying the amount of pressure that may be created by bellow pump 1310.

Figure 14:
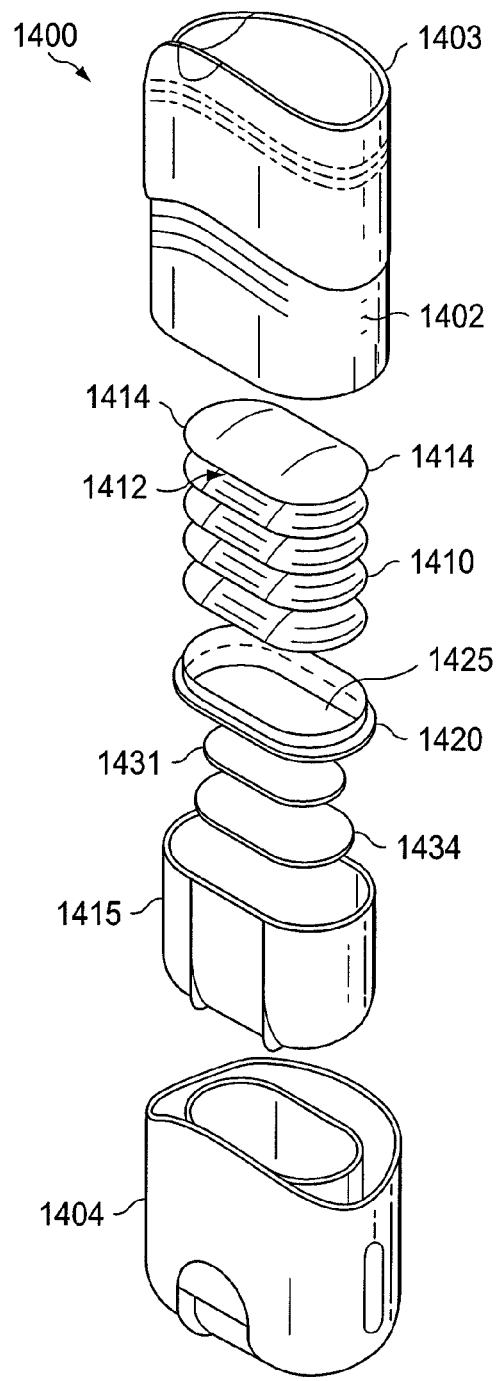
FIG. 14 illustrates a perspective view of an apparatus for applying reduced pressure at a tissue site in accordance with an illustrative embodiment.

Referring to FIG. 14, reduced pressure treatment system 1400, which is encased by a casing having a top casing portion 1402 and a bottom casing portion 1404, is shown in accordance with an illustrative embodiment. Reduced pressure treatment system 1400 compressible bellows 1410, filter housing 1420, odor filter 1431, hydrophobic filter 1434, and variable volume chamber 1415.

FIG. 14 shows the orientation of the different components of reduced pressure treatment system 1400 relative to one another. Compressible bellows 1410, which is a non-limiting example of compressible bellows 210 in FIG. 2, may be inserted into top casing portion 1402. Top casing portion also includes a grip 1403. Grip 1403 may be composed of rubber, plastic, or any other material capable of improving tactile grip on top casing portion 1402.

The cross-sectional shape of compressible bellows 1410 is an oval. In particular, compressible bellows 1410 has an elongated middle portion 1412 and rounded end portions 1414. The cross sectional shape of compressible bellows 1410 allows compressible bellows 1410 to fit into top casing portion 1402. The cross sectional shape of compressible bellows 1410 may vary depending on the shape of the casing for the reduced pressure treatment system.

Compressible bellows 1410 couples to filter housing 1420, which is a non-limiting example of filter housing 220 in FIG. 2. Filter housing 1420 includes a grid mesh 1425 through which gas may flow.

Odor filter 1431 and hydrophobic filter 1434, which are non-limiting examples of odor filter 231 and hydrophobic filter 234 in FIG. 2, respectively, fit into filter housing 1420 as described in the previous Figures. Fixed volume chamber 1415, which is a non-limiting example of fixed volume chamber 215 in FIG. 2, couples to filter housing 1420. Fixed volume chamber 415 may be inserted into bottom casing portion 1404.

Top casing portion 1402 and bottom casing portion 1404 may be composed of any material. For example, top casing portion 1402 and bottom casing portion 1404 may be composed of materials that are suitable to protect the inner components of reduced pressure treatment system 1400. Non-limiting examples of the material from which top casing portion 1402 and bottom casing portion 1404 may be composed include plastic, metal, or rubber.

Figure 15:
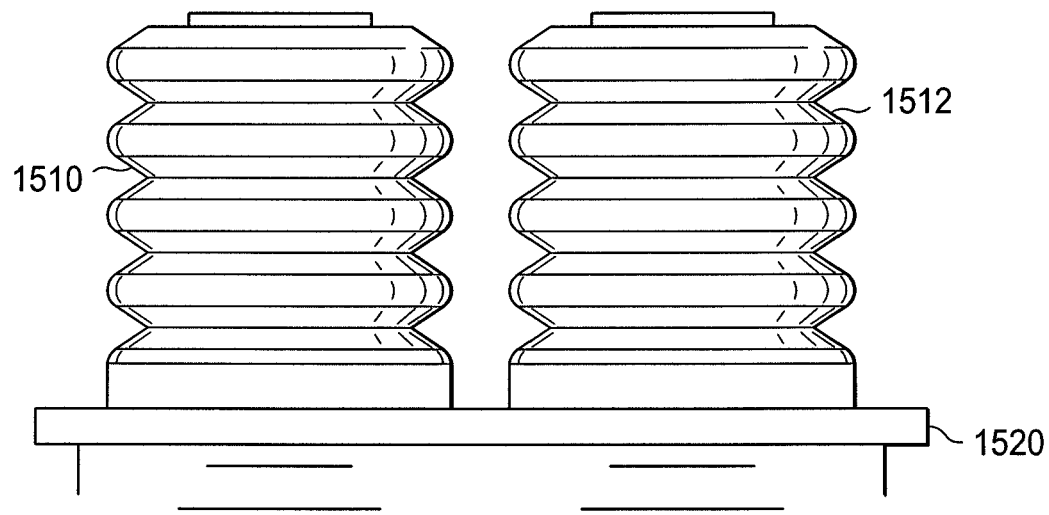
FIG. 15 illustrates a perspective view of two compressible pumps in an apparatus for applying reduced pressure at a tissue site in accordance with an illustrative embodiment.

Referring to FIG. 15, compressible bellows 1510 and 1512, each of which is a non-limiting example of compressible bellows 210 in FIG. 2, is shown in accordance with an illustrative embodiment. Compressible bellows 1510 and 1512 can replace the oval compressible bellows 1410 in FIG. 14. Thus, compressible bellows 1510 and 1512 may be configured to be inserted into a top casing portion, such as top casing portion 1402 in FIG. 14. Each of compressible bellows 1510 and 1512 are coupled to filter housing 1520, which is a non-limiting example of filter housing 1420 in FIG. 14.

The use of two compressible bellows 1510 and 1512 allows the reduced pressure treatment system in which compressible bellows 1510 and 1512 are employed to continue functioning in the event that one of the compressible bellows leaks or otherwise fails. The use of compressible bellows 1510 and 1512 may also improve manufacturing efficiency in the construction of a reduced pressure treatment system. For example, the manufacture of compressible bellows 1510 and 1512 having a circular cross-section may be easier than the manufacture of a single compressible bellows having an elongated cross section that allows the single compressible bellows to fit inside top casing portion 1402.

Figure 16:
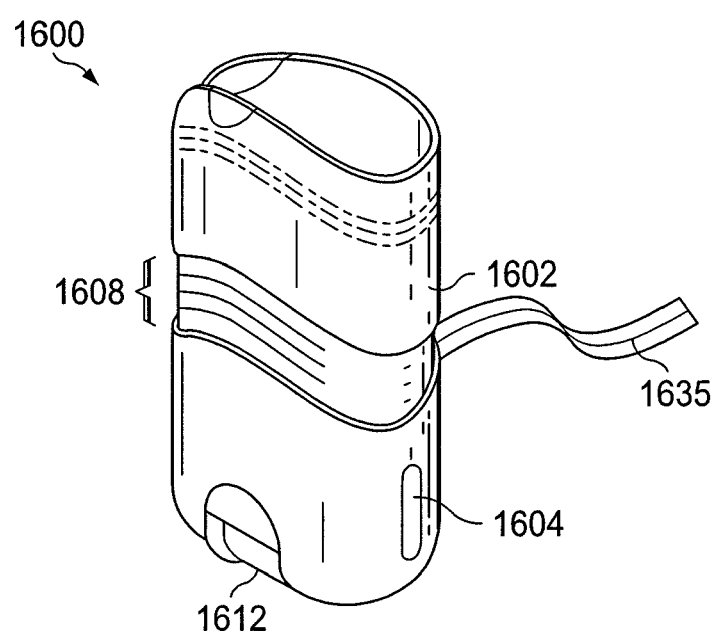
FIG. 16 illustrates a perspective view of an apparatus for applying reduced pressure at a tissue site in accordance with an illustrative embodiment.

Referring to FIG. 16, reduced pressure treatment system 1600, which is a non-limiting example of reduced pressure treatment system 1400 in FIG. 14, is shown in accordance with an illustrative embodiment. Reduced pressure treatment system 1600 shows reduced pressure treatment system 1400 when reduced pressure treatment system 1400 has been assembled. In reduced pressure treatment system 1600, top and bottom casing portions 1602 and 1604 encase the various components of reduced pressure treatment system 1600, such as a compressible bellows, filter housing, odor filter, hydrophobic filter, and fixed volume chamber. Top and bottom casing portions 1602 and 1604 are non-limiting examples of top and bottom casing portions 1402 and 1404 in FIG. 14, respectively.

Reduced pressure treatment system 1600 also includes visual indicators 1608. Visual indicators 1608 indicate to a user an amount of reduced pressure to be delivered to a tissue site, such as tissue site 105 in FIG. 1. In particular, the lines of visual indicators 1608 indicate the degree to which top casing portion 1602 has been compressed relative to bottom casing portion 1604, and therefore also indicates the degree to which the one or more compressible bellows inside top casing portion 1602 has been compressed. Using visual indicators 1608, a user can consistently deliver a desired amount of reduced pressure to a tissue site. The visual indicators 1608 may be located on either or both of the top casing portion 1602 or the bottom casing portion 1604.

Reduced pressure treatment system 1600 also includes an end cap 1612. End cap 1612 fits onto bottom casing portion 1604 and may be coupled to delivery tube 1635, which is a non-limiting example of delivery tube 135 in FIG. 1. Additional details regarding end cap 1612 will be described in FIGS. 19 and 20 below.

Figure 17A:
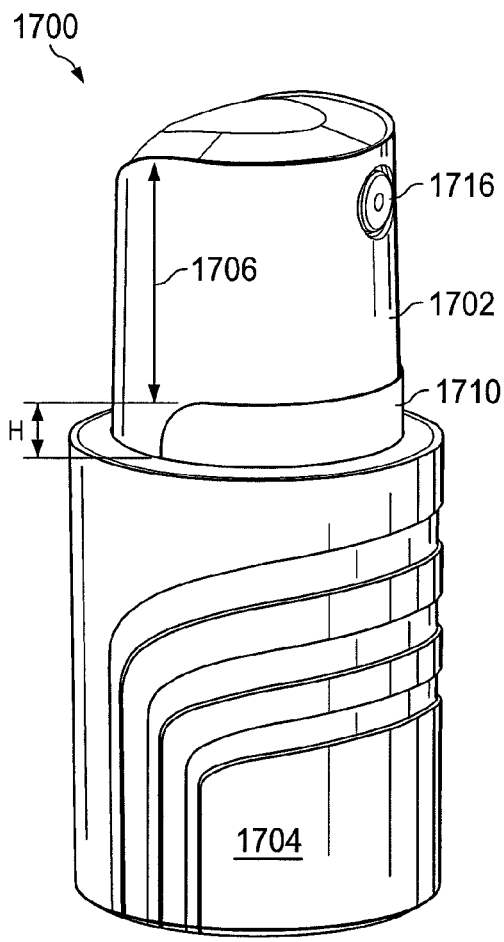
FIG. 17a illustrates a perspective view of an apparatus for determining a reduced pressure associated with a reduced pressure source in accordance with an illustrative embodiment.
Figure 17B:
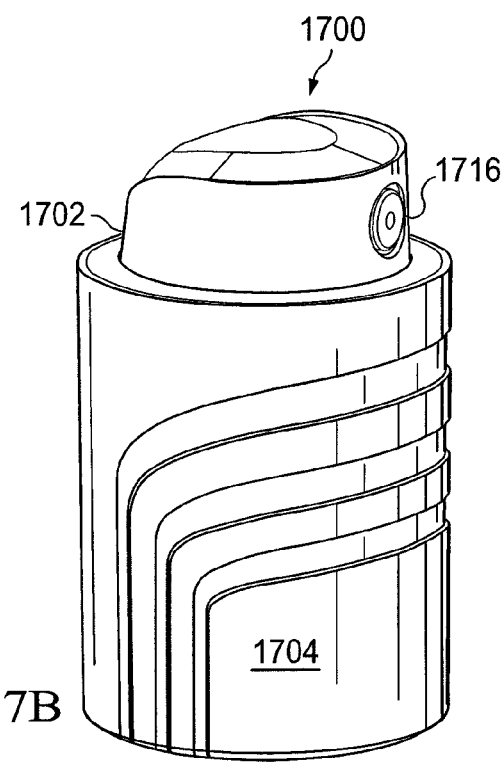
FIG. 17b shows a side view of the apparatus of FIG. 17a in the compressed position.
Figure 17C:
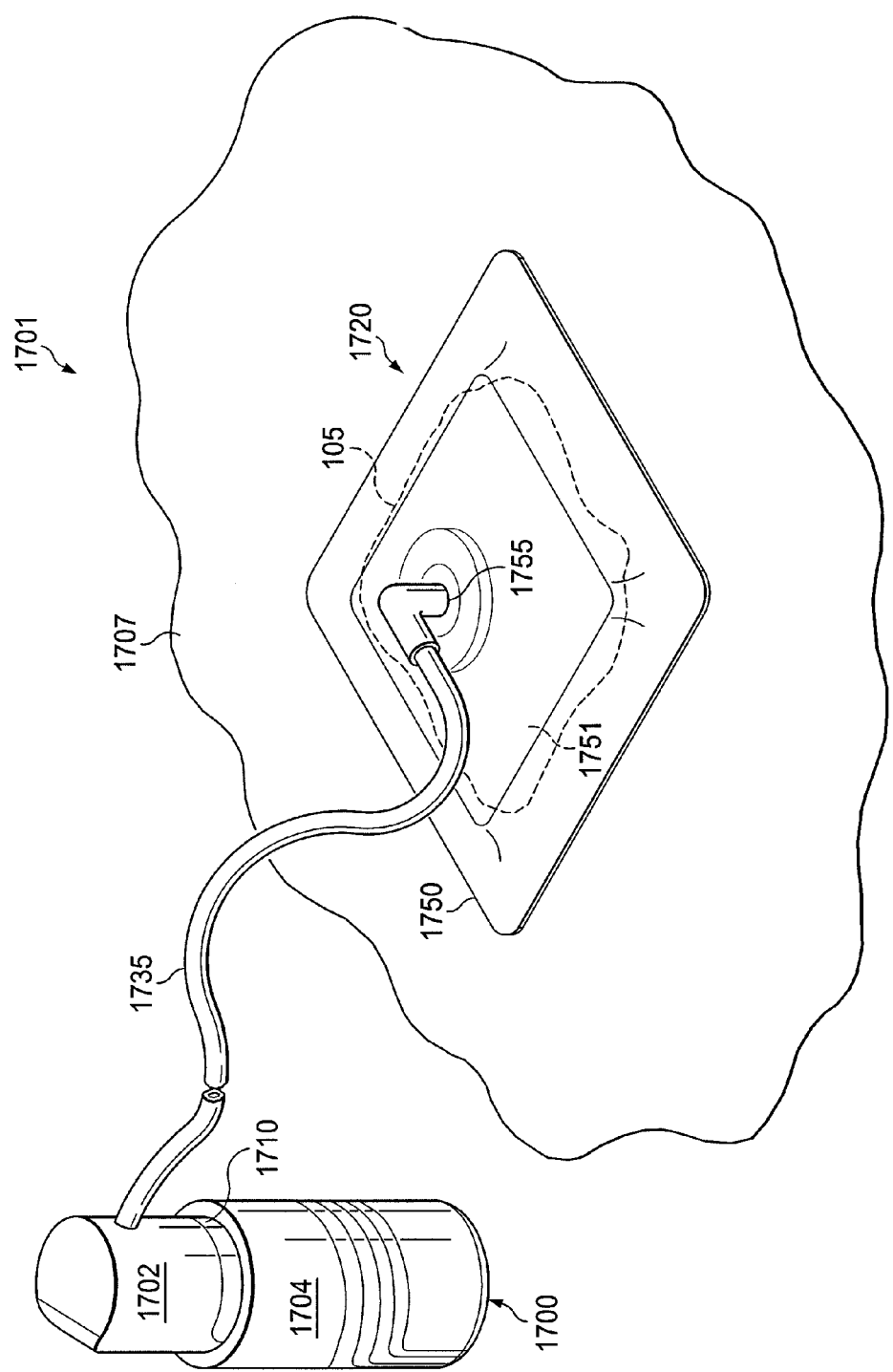

Referring to FIGS. 17a, 17b, and 17c, a reduced pressure apparatus 1700 includes a top casing portion 1702 and a bottom casing portion 1704, each of which have a substantially cylindrical shape. The bottom casing portion 1704 has a larger diameter than the top casing portion 1702 such that the top casing portion 1702 can be slidingly received by the bottom casing portion 1704. The top casing portion 1702 is compressible into a plurality of positions relative to the bottom casing portion 1704, including the uncompressed position shown in FIG. 17a, the fully compressed position shown in FIG. 17b, and a plurality of intermediate positions (which are partially compressed) between the uncompressed position and the fully compressed position. The top casing portion 1702 may be slidable into the bottom casing portion 1704 along an axis substantially parallel to bidirectional arrow 1706.

The top casing portion 1702 includes an indicator 1710. The indicator 1710 is disposed on a region of the top casing portion 1702 that is adjacent the bottom casing portion 1704 when the reduced pressure apparatus 1700 is in the uncompressed position. The indicator 1710 is visible when the top casing portion 1702 is in the uncompressed position but is obscured, or not visible, when the top casing portion 1702 is in the fully compressed position. The indicator 1710 may also be visible in at least one of the intermediate positions between the compressed position and the uncompressed position.

In another embodiment, the visual indicators described herein may be provided to indicate when the reduced pressure apparatus is in a fully compressed position prior to a first use of the reduced pressure apparatus. Such an indicator would assist in ensuring that the reduced pressure apparatus is fully charged or that the reduced pressure apparatus is not being reused on another patient.

The indicator 1710 may be any indicia or markings that is capable of indicating a position of the top casing portion 1702 relative to the bottom casing portion 1704. In the embodiment illustrated in FIG. 17, the indicator 1710 is a color band or color strip that is a contrasting color to the color of adjacent portions of the top casing portion 1702. The color of the indicator 1710 may be any color or multiple colors. Alternatively, the indicator 1710 may not be a solid color band, but instead may be an outline of a band or strip. Similarly, the indicator 1710 may be a region on the top casing portion 1702 that includes striping, letters, numbers, symbols, or other indicia. In FIG. 17a, the indicator 1710 is partially disposed around the circumference of the top casing portion 1702, but the indicator 1710 may also be disposed around an entire circumference of the top casing portion 1702.

In another embodiment, the indicator 1710 is a tactile indicator that has a texture that is different from the texture of the remainder of the top casing portion 1702. In this embodiment, a visually-impaired user may touch the top casing portion 1702 to determine the position of the reduced pressure apparatus 1700. When the reduced pressure apparatus 1700 is in the uncompressed position, the user will be able to feel the indicator 1710 and thereby be notified that the system 1710 is in the uncompressed position.

In operation, the reduced pressure apparatus 1700 is manually actuated to generate a reduced pressure at an outlet 1716. Manual actuation of the reduced pressure apparatus 1700 is accomplished by a user manually compressing the top casing portion 1702 within the bottom casing portion 1704 such that the top casing portion 1702 is placed in the fully compressed position or at least one of the intermediate positions. The internal mechanism for generating reduced pressure may be any suitable mechanism including, without limitation, those mechanisms that have been described herein. In at least one embodiment, the mechanism by which reduced pressure is generated involves the reduction in volume of and expulsion of gas from a chamber (not shown), and then subsequently a sealing of the chamber and expansion in volume of the chamber. As the volume of the sealed chamber increases, the reduced pressure is generated within the chamber. The reduction in volume of the chamber may be accomplished by compressing the top casing portion 1702 within the bottom casing portion 1704.

FIG. 17c shows the reduced pressure apparatus 1700 as part of a reduced pressure therapy system 1701. The reduced pressure apparatus 1700 is fluidly coupled to a dressing 1720 via a conduit 1735 that delivers reduced pressure. A sealing member 1750 covers the tissue site 105 of a patient 1707. The sealing member 1750 has an aperture in which the connection member 1755 is disposed. The conduit 1735 is in fluid communication with a sealed space 1751 that is covered by the sealing member 1750 via the connection member 1755. The dressing 1720 may also include a manifold in the sealed space 1751. Reduced pressure may be delivered to the sealed space 1751 by the reduced pressure apparatus 1700.

When the top casing portion 1702 is placed in the fully compressed position, the indicator 1710 is no longer visible since the portion of the top casing portion 1702 on which the indicator 1710 lies is hidden from view within the bottom casing portion 1704. When fully compressed, reduced pressure is delivered to an outlet 1716, and this reduced pressure is available for delivery the tissue site 105. As time passes, air leakage from the sealed space 1751, as well as other factors that cause local increases in pressure at the tissue site 105, results in a movement of the top casing portion 1702 toward the uncompressed position. As the top casing portion 1702 moves closer to the uncompressed position, the indicator 1710 begins to become exposed. Since movement toward the uncompressed position indicates a loss of reduced pressure, or a loss of remaining capacity to generate reduced pressure, the presence of the indicator 1710 communicates to a user that a partial discharge of the reduced pressure apparatus 1700 has occurred. The presence of the visual indicator 1710 further communicates to the user the approaching need to re-charge or re-compress the reduced pressure apparatus 1700 back into a compressed position in order to deliver or maintain a therapeutic reduced pressure at the tissue site 105. If the rate of discharge of the reduced pressure apparatus 1700 is constant, the initial presence of the indicator 1710 at an intermediate position may be determinative of the amount of time remaining during which reduced pressure will be generated or applied.

The indicator 1710 includes a height, H, in a direction parallel to the direction of travel of the top casing portion 1702 indicated by bidirectional arrow 1706. The height, H, is determinative of when the indicator 1710 will first be exposed during operation of the reduced pressure apparatus 1700. As the reduced pressure apparatus 1700 discharges and the top casing portion moves from the fully compressed position to the uncompressed position, an indicator having a greater height will be visible earlier than an indicator having a lesser height.

As explained above, the indicator 1710 is capable of communicating the approaching cessation of reduced pressure generation or delivery, and in some cases, the amount of time left until such cessation. The indicator 1710 may also be capable of alerting a user that a particular amount of reduced pressure is being applied. In one example, the compression of the top casing portion 1702 into a compressed position decreases the volume of a variable volume chamber located in the bottom casing portion 1704. The reduced pressure in the variable volume chamber in the bottom casing portion 1704 may decrease as the top casing portion 1702 moves toward an uncompressed position. As the top casing portion 1702 moves through the intermediate positions toward the uncompressed position, the indicator 1710 becomes more exposed. The relative positioning of the top casing portion 1702 and the bottom casing portion 1704 at the time the indicator 1710 is first exposed, and at times subsequent to the first exposure, may be indicative of a particular reduced pressure, which may be communicated to the user by the presence and positioning of the indicator 1710.

Figure 18:
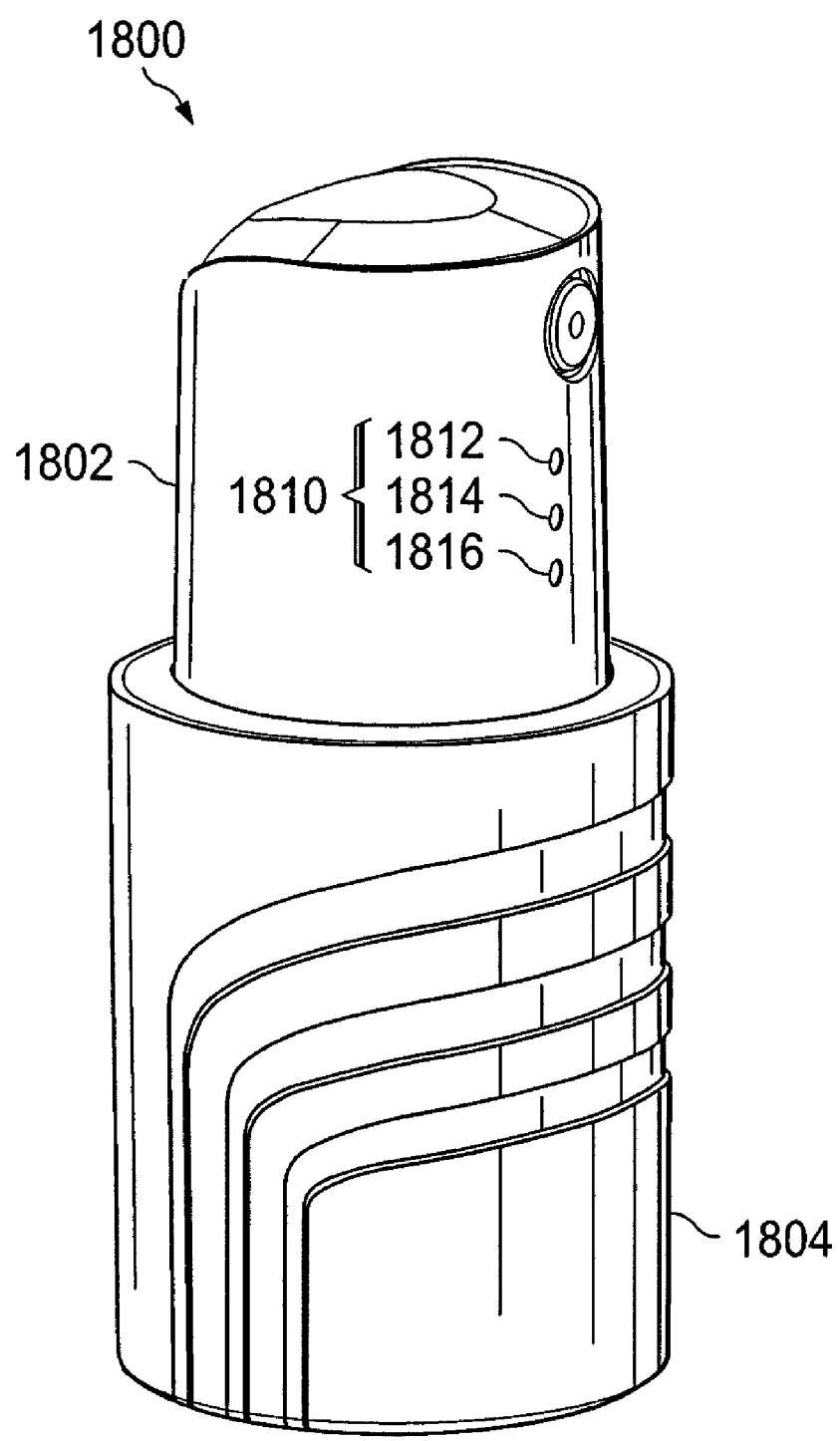
FIG. 18 illustrates a perspective view of an apparatus for determining a reduced pressure associated with a reduced pressure source in accordance with an illustrative embodiment.

Referring to FIG. 18, a reduced pressure treatment system 1800 is shown according to an illustrative embodiment. The reduced pressure treatment system 1800, in contrast to the reduced pressure apparatus 1700, includes indicia or markings 1810. Although each of the markings 1810 are shown to be circles, each of the markings 1810 may have any shape, such as a square, a triangle, or other polygon. Alternatively, the markings 1810 may be lines, symbols, numbers, or letters, or some combination thereof. In the embodiment in which the markings 1810 are lines, the lines may be substantially perpendicular to the axis along which the top casing portion 1802 is compressible. Although the plurality of markings 1810 includes three markings, the plurality of markings 1810 may include any number of markings. When the top casing portion 1802 is compressed into the bottom casing portion 1804, all or a portion of the plurality of markings 1810 are hidden from view.

As the top casing portion 1802 moves toward an uncompressed position, each of the plurality of markings 1810 may gradually become exposed. For example, as the top casing portion 1802 moves toward an uncompressed position from a fully compressed position, the marking 1812 may first become exposed. The marking 1814 may then become exposed as the top casing portion 1802 moves further toward the uncompressed position. Finally, the marking 1816 may then become exposed as the top casing portion 1802 moves into a fully uncompressed position. Each of the plurality of markings 1810 may have a different color or texture to provide a user with color or tactile-aided indications of the position of the top casing portion 1802.

The user may be alerted to a state of the reduced pressure treatment system 1800 based on the number of the plurality of markings 1810 that are exposed to the user. For example, the more of the plurality of markings 1810 that are exposed, the more urgent may be the need for a user to perform an action to the reduced pressure treatment system 1800, such as to compress the top casing portion 1802 into a compressed position to maintain a reduced pressure that is being generated or delivered by the reduced pressure treatment system 1800.

Figure 19:
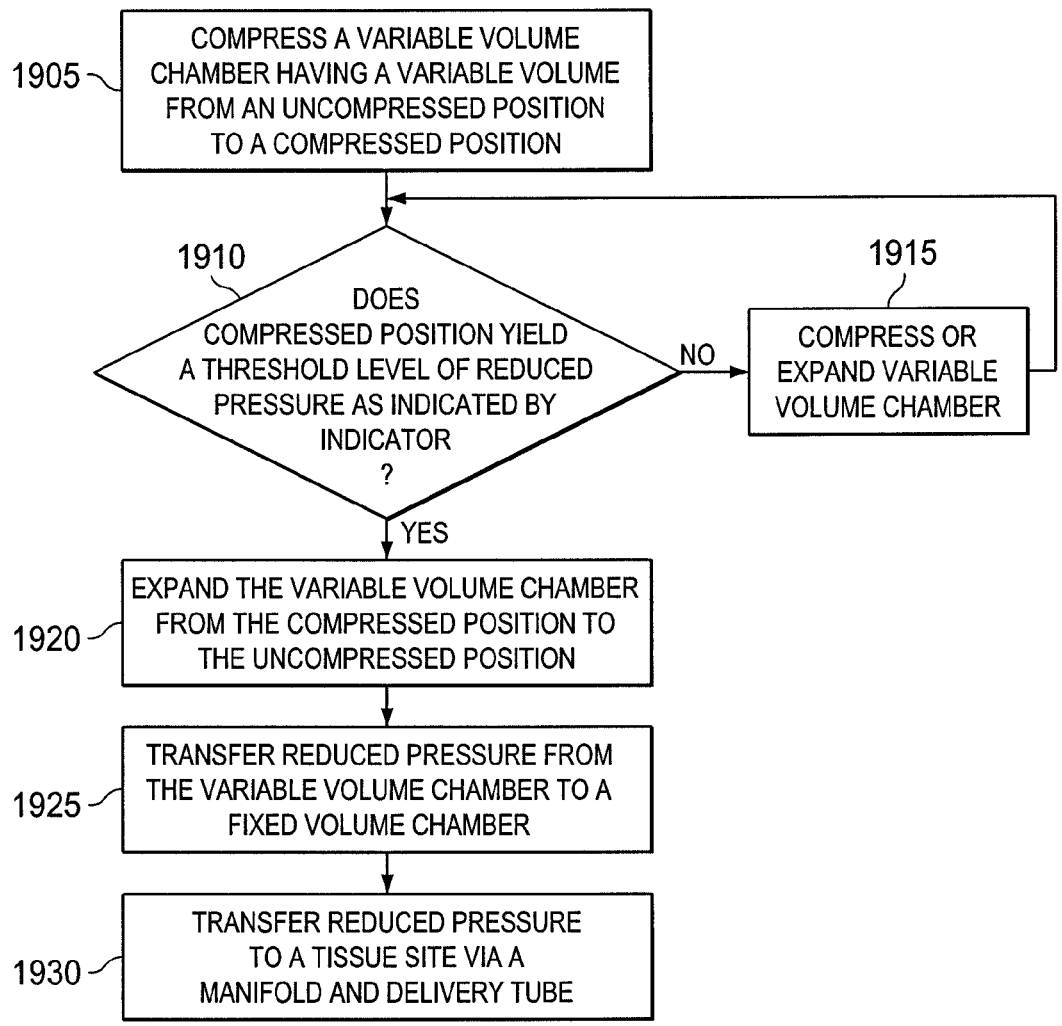
FIG. 19 illustrates a flowchart illustrating a process for applying reduced pressure at a tissue site in accordance with an illustrative embodiment.

Referring to FIG. 19, a process that may be implemented by a manually-actuated pump, such as pump 102 in FIG. 1 or any other illustrative embodiment of the reduced pressure treatment system described above, is shown in accordance with an illustrative embodiment.

The process compresses a variable volume chamber having a variable volume from an uncompressed position to a compressed position (step 1905). The process determines whether the compressed position yields a threshold level of reduced pressure as indicated by an indicator, such as visual indicators 1608 in FIG. 16 (step 1910). If the process determines that the compressed position does not yield a threshold level of reduced pressure as indicated by an indicator, the process further compresses or expands the variable volume chamber (step 1915). The process then returns to step 1910.

If the process determines that the compressed position yields a threshold level of reduced pressure as indicated by an indicator, the process may then expand the variable volume chamber from the compressed position to the uncompressed position (step 1920). The process transfers reduced pressure from the variable volume chamber to a fixed volume chamber (step 1925). The process may then transfer the reduced pressure to a tissue site via a manifold and delivery tube (step 1930).

The flowcharts and block diagrams in the different depicted embodiments illustrate the architecture, functionality, and operation of some possible implementations of the apparatus and methods. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The illustrative embodiments described herein separate the chambers in which exudates and other liquids are collected from the reduced-pressure-generating chamber. Thus, the compressible pumps are capable of being re-charged (i.e. the flexible bellows can be re-depressed) even when liquids are present in the fixed volume chamber. When the fixed volume chamber becomes completely full of exudate or other liquids, the fixed volume chamber may then be emptied before additional reduced pressure may be applied by the compressible pump. Also, the illustrative embodiments, unlike traditional manually-activated systems, are capable of delivering a measured and consistent amount of pressure to a tissue site during a particular reduced pressure treatment cycle. The illustrative embodiments are further capable of consistently repeating the targeted pressure each time the compressible pump is recharged. These pressure delivery capabilities exist regardless of the orientation or location of the fixed volume chamber.

The illustrative embodiments are also capable of alerting a user as to the need to perform an action on a reduced pressure source. For example, the illustrative embodiments may include a visual indicator that, when exposed, alerts a user that the reduced pressure source needs to be compressed or otherwise charged.

We claim:

1. A reduced pressure apparatus comprising:
   a first casing portion;
   a second casing portion slidably coupled to the first casing portion such that the first casing portion is compressible into a plurality of positions relative to the second casing portion, the plurality of positions including a fully compressed position and a fully uncompressed position; and
   an indicator disposed on at least one of the first casing portion and the second casing portion, the indicator being exposed when the first casing portion is in the fully uncompressed position and being obscured when the first casing portion is in the fully compressed position;
   wherein the reduced pressure apparatus is configured to deliver a reduced pressure to a tissue site when the first casing portion is in the fully compressed position.

2. The reduced pressure apparatus of claim 1, wherein the indicator is located on a region of the first casing portion that is adjacent the second casing portion when the first casing portion is in the uncompressed position.

3. The reduced pressure apparatus of claim 2, wherein the indicator is a strip that is at least partially circumferentially disposed around the first casing portion.

4. The reduced pressure apparatus of claim 3, wherein the strip is disposed around an entire circumference of the first casing portion.

5. The reduced pressure apparatus of claim 3, wherein a color of the strip is different than a color of the remainder of the first casing portion.

6. The reduced pressure apparatus of claim 1, wherein the indicator is a plurality of markings.

7. The reduced pressure apparatus of claim 6, wherein the plurality of markings are located along an axis, wherein the first casing portion is compressible along the axis.

8. The reduced pressure apparatus of claim 7, wherein the plurality of markings is a plurality of circles.

9. The reduced pressure apparatus of claim 7, wherein the plurality of markings is a plurality of lines, each of the lines being substantially perpendicular to the axis.

10. The reduced pressure apparatus of claim 6, wherein each of the plurality of markings have a different color.

11. The reduced pressure apparatus of claim 1, wherein the indicator has a texture that is different than a texture of the remainder of the first casing portion.

12. The reduced pressure apparatus of claim 1, wherein the indicator is exposed when the first casing portion is in an intermediate position between the fully compressed position and the fully uncompressed position.

13. A reduced pressure therapy system for administering reduced pressure treatment to a tissue site, the system comprising:
    a manifold adapted to be positioned at the tissue site;
    a reduced pressure source in fluid communication with the manifold to deliver a reduced pressure to the manifold, the reduced pressure source comprising: a top casing portion;
    a bottom casing portion slidably coupled to the top casing portion such that the top casing portion is positionable in a plurality of positions relative to the bottom casing portion, the plurality of positions including a fully compressed position, a fully uncompressed position, and a plurality of intermediate positions between the fully compressed position and the fully uncompressed position, wherein the reduced pressure source operable to delivers the reduced pressure when the top casing portion is in the fully compressed position; and
    an indicator disposed on at least one of the top casing portion and the bottom casing portion, the indicator being exposed when the top casing portion is in at least one of the plurality of intermediate positions and being obscured when the first casing portion is in the fully compressed position; and
    a sealing member adapted to cover the tissue site to form a sealed space between the sealing member and the tissue site, the sealed space in fluid communication with the reduced pressure source.

14. The reduced pressure therapy system of claim 13, wherein the top casing portion moves toward a fully uncompressed position as gas leaks from the sealed space.

15. The reduced pressure therapy system of claim 13, wherein the reduced pressure source is operable to deliver the reduced pressure to the sealed space when the top casing portion is in at least one of the plurality of intermediate positions.

16. The reduced pressure therapy system of claim 13, wherein the indicator is located on a region of the top casing portion that is adjacent the bottom casing portion when the top casing portion is in the fully uncompressed position.

17. The reduced pressure therapy system of claim 13, wherein the indicator is a strip that is at least partially circumferentially disposed around the top casing portion.

18. A reduced pressure apparatus comprising:
    a substantially cylindrical top casing portion;
    a substantially cylindrical bottom casing portion having a larger diameter than the substantially cylindrical top casing portion, the substantially cylindrical top casing portion slidably received by the substantially cylindrical bottom casing portion such that the substantially cylindrical top casing portion is positionable in a plurality of positions relative to the substantially cylindrical bottom casing portion, the plurality of positions including a fully compressed position, a fully uncompressed position, and a plurality of intermediate positions between the fully compressed position and the fully uncompressed position, the reduced pressure apparatus configured to deliver a reduced pressure to a tissue site as the substantially cylindrical top casing portion moves from the fully compressed position to the fully uncompressed position; and a color strip disposed on the substantially cylindrical top casing portion such that the color strip is exposed when the substantially cylindrical top casing portion is in the fully uncompressed position and is obscured when the substantially cylindrical top casing portion is in the fully compressed position.

19. The reduced pressure apparatus of claim 18, wherein the color strip is exposed when the substantially cylindrical top casing portion is in at least one of the plurality of intermediate positions.

* * * * *